(12) United States Patent
Kito et al.

(10) Patent No.: US 7,081,107 B2
(45) Date of Patent: Jul. 25, 2006

(54) SYRINGE AND PREFILLED SYRINGE

(75) Inventors: Hideaki Kito, Nakakoma-gun (JP); Kouichi Tachikawa, Nakakoma-gun (JP); Masaaki Kasai, Nakakoma-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 8 days.

(21) Appl. No.: 10/519,705

(22) PCT Filed: Jul. 2, 2003

(86) PCT No.: PCT/JP03/08413

§ 371 (c)(1),
(2), (4) Date: Dec. 30, 2004

(87) PCT Pub. No.: WO2004/004811

PCT Pub. Date: Jan. 15, 2004

(65) Prior Publication Data

US 2005/0240159 A1    Oct. 27, 2005

(30) Foreign Application Priority Data

Jul. 2, 2002    (JP) .............................. 2002-194010
Jul. 26, 2002   (JP) .............................. 2002-218140
Sep. 11, 2002   (JP) .............................. 2002-266000

(51) Int. Cl.
*A61M 5/315* (2006.01)
(52) U.S. Cl. ...................... 604/221; 604/218
(58) Field of Classification Search ................ 604/218, 604/219, 221, 231
See application file for complete search history.

(56) References Cited

U.S. PATENT DOCUMENTS 404,105 A * 5/1889 Overlach .................... 604/221
4,632,672 A * 12/1986 Kvitrud ...................... 604/222
4,813,938 A * 3/1989 Raulerson ................... 604/158
5,330,443 A * 7/1994 Powles et al. .............. 604/240

FOREIGN PATENT DOCUMENTS

| EP | 0 304 386 A2 | 2/1989 |
| EP | 0 526 824 A2 | 2/1993 |
| JP | 115681/1978 | 9/1978 |
| JP | 1-254169 | 10/1989 |
| JP | 91353/1991 | 9/1991 |
| JP | 7-246238 | 9/1995 |
| WO | WO 95/11711 A1 | 5/1995 |

OTHER PUBLICATIONS

International Search Report PCT/ISA/210.

* cited by examiner

*Primary Examiner*—Sharon Kennedy
(74) *Attorney, Agent, or Firm*—Buchanan Ingersoll PC

(57) ABSTRACT

A syringe (and a prefilled syringe) of a structure with ventilation means allowing a pusher to be easily pushed or pulled in use, providing an excellent operability of discharging (injecting) chemicals, making it hard for foreign matter such as dirt and dust to enter into a syringe outer tube when not in use during storage or transporation, capable of assuring, by itself, the sanitation of the syringe outer tube when not in use, and allowed to be shipped without individually packaging the syringe with packaging material, wherein, as more desirable embodiments, the aseptic condition in the outer tube can be surely maintained even if the push and pull operations of the pusher are performed and, even if the pusher is pushed when not in use, a gasket does not move in tip direction and the arrangement of the pusher at the time of shipping can be stably maintained.

17 Claims, 19 Drawing Sheets

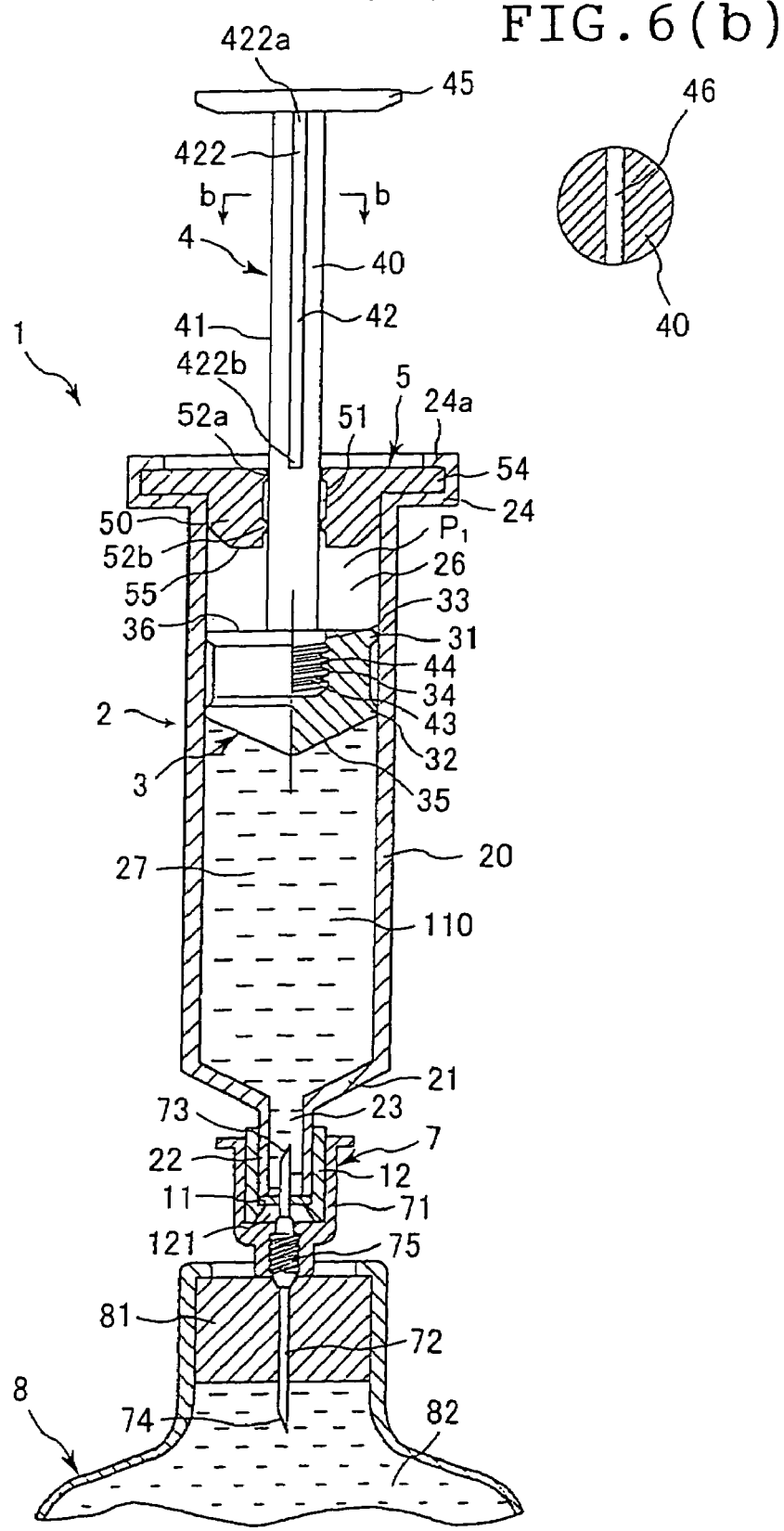

FIG.7(a)
FIG.7(b)
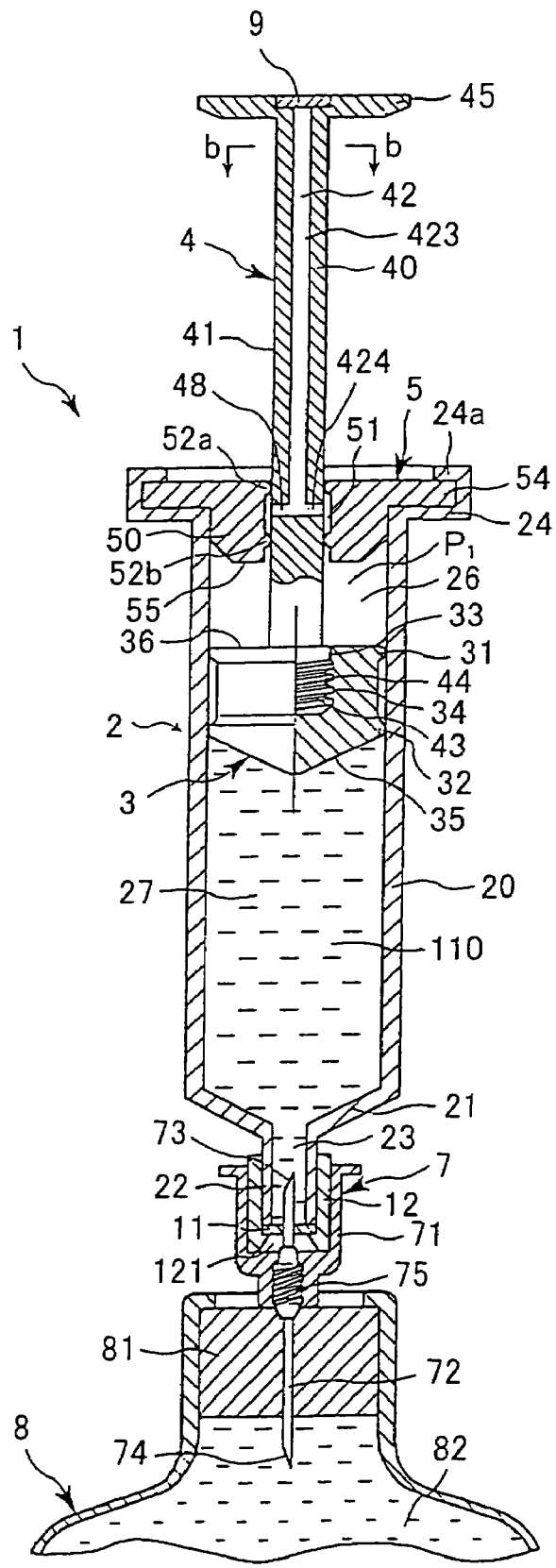
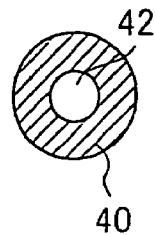

SYRINGE AND PREFILLED SYRINGE

TECHNICAL FIELD

The present invention relates to a syringe and a prefilled syringe in which a chemical is preliminarily contained.

BACKGROUND ART

A syringe is generally composed of an outer tube provided on the tip end side thereof with a mouth portion reduced in diameter, a gasket inserted in the outer tube via a base end opening of the outer tube, and a pusher (plunger rod) connected to the gasket.

A prefilled syringe with a chemical preliminarily contained (sealed) in a syringe is known. The chemical usually is aseptically sealed in a space (first space) on the tip end side relative to the gasket maintained in a hermetically closed condition by a seal at the mouth portion. In using the prefilled syringe containing a liquid chemical as a chemical, for example, the outer tube is usually held by one hand, and the pusher is pushed by the other hand to slide the gasket in the outer tube to the tip end direction, thereby discharging (injecting) the liquid chemical via the mouth portion. Besides, where the chemical is a powdery chemical, usually, the pusher is once pulled to slide the gasket to the base end direction, and a liquid such as an injection is sucked into the first space via the mouth portion of the outer tube, thereby dissolving the chemical to form a liquid chemical, and the pusher is then pushed so as to discharge the liquid chemical.

The pusher of a commercially available syringe (prefilled syringe) generally has a main body portion having a cross section shaped like a cross, with tip end portions of the cross abutting on the inside wall of the outer tube. Therefore, the gap (second space) between the outer tube inside wall and the pusher on the base end side relative to the gasket is in an open condition and, when the open condition is kept as it is, foreign matter such as dirt and dust may enter into the second space together with the outside air or bacterial pollution may occur during storage, transportation or the like, which is disadvantageous on a sanitary basis. Therefore, the syringe is usually shipped as a product aseptically packaged with a packaging material.

In using such a packaged syringe, the space in the outer tube on the tip end side relative to the gasket is maintained in the aseptic hermetically closed condition until a mouth portion seal is unsealed even after the packaging material is opened, whereas the outside air flows into the space on the base end side relative to the gasket simultaneously when the packaging material is opened.

In view of this, a syringe with a cap attached to the base end of the non-used syringe is also known. For example, in a prefilled syringe proposed in Japanese Patent Laid-open No. Hei 7-246238 wherein a medical drug and a diluting liquid are sealed respectively in an outer tube and an inner tube (piston rod) and individually stored there, the base ends of the outer tube and the inner tube are sealed with caps, respectively. This configuration ensures that, when not in use during storage or transportation, the outside air is blocked from flowing into the spaces in the outer tube and the inner tube on the base end side relative to the piston (gasket).

However, the prefilled syringe of the type in which the outer tube and the inner tube are individually sealed with caps has the disadvantage that the operation at the time of using it is intricate and troublesome, since an operation of removing the caps is needed and it is necessary to attach an inner tube tip end portion to the piston in the outer tube and to attach another pushing rod (pusher) to a base end portion of the inner tube (see FIG. 2 of the above-mentioned publication). In order to improve the intricateness at the time of use, i.e., removal of the caps and attachment of the pusher, it may be contemplated to provide each of the caps for the outer tube and the inner tube with a hole and to insert the inner tube and the pusher into the holes in a gas-tight condition, thereby integrating the prefilled syringe.

However, the gas-tight sealing on the base end side of the outer tube as above-mentioned makes it difficult to push the pusher for discharging the liquid. This is because the pressure inside the space in the outer tube on the base end side relative to the gasket is lowered, attendant on the operation to push the pusher for sliding the gasket inside the outer tube to the tip end direction so as to discharge or inject the liquid, with the result that a force for pushing back the gasket (pusher) to the base end direction is exerted.

In addition, the syringe is shipped in the state of being packaged as above-mentioned, so that, when the pusher is pushed by some force and the gasket is thereby moved inside the outer tube to the tip end direction during transportation or storage, the following troubles are generated.

1) By being pushed by the gasket moved, a cake (a certain-shaped freeze-dried preparation) of a chemical may be collapsed, thereby spoiling the beautiful appearance of the product.

2) Due to the movement of the gasket to the tip end direction, the collapsed powdery chemical (or a chemical being in a powdery form from the beginning) may enter into the gap between the outer circumferential surface of the gasket and the inner circumferential surface of the outer tube. If the chemical has entered into the gap, at the time of feeding the chemical by use of the syringe, the chemical having entered into the gap may be left undissolved in the liquid sucked into the outer tube, causing an error in the amount of the chemical fed.

3) Where the presealed chemical is a liquid (liquid chemical), when the gasket is going to move to the tip end direction, the pressure of the liquid chemical is increased, with the result that the liquid may leak out by breaking the sealing member at the mouth portion or may leak to the base end side of the gasket via the gap between the outer circumferential surface of the gasket and the inner circumferential surface of the outer tube.

DISCLOSURE OF INVENTION

It is an object in a broad sense of the present invention to provide a syringe structure and a prefilled syringe capable of assuring, by themselves, the sanitation of a syringe outer tube when not in use, allowed to be shipped without being individually packaging with a packaging material, and providing excellent operability of discharging (injecting) liquid chemicals at the time of use.

Particularly, it is a first object of the present invention to provide a syringe and a prefilled syringe making it hard for foreign matter such as dirt and dust to enter into the syringe, assuring the sanitation of a syringe outer tube when not in use during storage, transportation or the like, preferably capable of obviating bacterial pollution, making it easy to push or pull a pusher in use, and making it easy to discharge (inject) liquid chemicals.

It is a second object of the present invention to provide a syringe and a prefilled syringe of a structure capable of surely maintaining the aseptic property of the inside of an outer tube even if the push and pull operations of a pusher are performed.

It is a third object of the present invention to provide a syringe and a prefilled syringe of a structure in which a gasket does not move to the tip end direction even if a pusher is pushed when not in use, and the arrangement of the pusher at the time of shipping is stably maintained.

In the present invention, the first object above is attained by a sealing member disposed at a base end opening of an outer tube, and a pusher having ventilation means slidably fitted in an insertion hole provided at the center of the sealing member. Specifically, as a first-named invention, there is provided a syringe structure including a hollow cylindrical outer tube, a gasket disposed in the outer tube to partition the space inside the outer tube into the tip end side and the base end side, and a pusher connected to the gasket, wherein at least a barrel portion, on the side of connection to the gasket, of the pusher is in the form of a hollow cylinder making close contact with the hole in the sealing member, the ventilation means as will be described later is provided along the axial direction, the sealing member provided with the insertion hole in its center is disposed at the base end opening of the outer tube, and the pusher is slidably fitted in the insertion hole.

Examples of the ventilation means include a rugged shape such as a groove, slit or rib provided in or on the outer circumference of a barrel portion (solid) on the base end side of the pusher, for providing a gap between the sealing member and the insertion hole, and a structure in which the pusher is a hollow cylinder over the entire part in the axial direction.

In the syringe having such ventilation means, the space formed inside the outer tube by the inner circumferential surface of the outer tube and the outer circumferential surface of the pusher on the base end side relative to the gasket can be opened or closed by moving the pusher forwards (pushing) or backwards.

The second object above is attained by the mode of including the pusher of the hollow cylindrical structure as the ventilation means as above-mentioned, wherein an end portion of a ventilation passage or a filter, particularly a sterilizing filter, is disposed at the tip end or base end opening portion of the pusher.

As a second-named invention for attaining the third object above, there is provided a syringe structure in which a finger receiving portion of a pusher is provided as a member (operating portion) separate from a pusher main body portion, the operating portion is engaged with the pusher main body portion in an expandable and contractible condition, and the tip end of the operating portion is stopped by a base end portion of an outer tube.

Further, a prefilled syringe with a chemical contained in a syringe of each above-mentioned structure is provided.

Specifically, the first object above is attained by a first mode of the present invention as shown in the following paragraphs (1) to (6).

(1) A syringe comprising: an outer tube provided on the tip end side thereof with an opening portion permitting a liquid to come in and out therethrough; a gasket slidable in the outer tube; a pusher connected to the gasket and operated to move the gasket in the longitudinal direction of the outer tube; ventilation means provided in the pusher; and a sealing member sealing a base end opening of the outer tube and having an insertion hole for inserting the pusher therethrough; wherein a first space surrounded by the outer tube and the gasket and located on the tip end side of the gasket and a second space surrounded by the outer tube, the gasket and the sealing member and located on the base end side of the gasket are provided in the outer tube, and before an operation to push the pusher to the tip end direction, the second space is maintained in the state of being shielded (sealed) from the outside air and, when the operation to push the pusher to the tip end direction is performed, the outside air is let into the second space via the ventilation means.

(2) A syringe as set forth in the above paragraph (1), wherein the ventilation means is a groove or slit opening to the outer circumferential surface of the pusher.

(3) A prefilled syringe as set forth in the above paragraph (1), wherein the ventilation means is comprised of a ventilation passage formed inside the pusher to open, at one end thereof, to the outer circumferential surface of said pusher.

(4) A syringe as set forth in the above paragraph (1), wherein the ventilation means is a rib formed on the outer circumferential surface of the pusher.

(5) A syringe as set forth in any of the above paragraphs (1) to (4), wherein the pressure difference $P_1-P_2$ is not more than 0.9 atm, where $P_1$ [atm] is the pressure in the second space before the start of the operation to push the pusher to the tip end direction, and $P_2$ [atm] is the pressure in the second space after the operation to push the pusher to the tip end direction is started and immediately before the outside air is let into the second space.

(6) A syringe as set forth in any of the above paragraphs (1) to (5), wherein the moving distance of the pusher from the time when the operation to push the pusher to the tip end direction is started till the time when the outside air is let into the second space is from 2 to 10 mm.

Besides, in the first-named invention, preferable examples for attaining also the second object include the invention as set forth in the following paragraphs (7) to (12), having a syringe structure in which the ventilation means includes a ventilation passage in the pusher as set forth in the above paragraph (3), wherein an end portion of the ventilation passage or a filter, particularly a bacteria-removing filter, is disposed at the tip end or a base end opening portion of the pusher.

(7) A syringe as set forth in any of the above paragraphs (3) to (6), wherein the ventilation means includes a filter at an end portion or an intermediate portion of the ventilation passage.

(8) A syringe as set forth in the above paragraph (7), wherein the filter is impermeable to bacteria.

(9) A syringe comprising: an outer tube provided on the tip end side thereof with a mouth portion permitting a liquid to come in and out therethrough;

a gasket slidably disposed in the outer tube and partitioning the inside of the outer tube into the tip end side and the base end side;

a pusher connected to the gasket and operated to move the gasket in the longitudinal direction of the outer tube; a ventilation passage formed inside the pusher so as to communicate a second space surrounded by the outer tube, the gasket and the sealing member and located on the base end side of the gasket and the exterior to each other; and a filter disposed so as to shut off the ventilation passage, and permitting gases to pass therethrough but not permitting bacteria to pass therethrough;

wherein when the pusher is moved to the tip end direction, the outer circumferential surface of the pusher slides while making close contact with at least a part of the insertion hole, and the outside air is let into the space through the ventilation passage.

(10) A syringe as set forth in the above paragraphs (9), wherein the gasket is provided with a hollow portion opening to a base end face thereof, the pusher is provided at a tip end portion thereof with a head portion to be inserted into the hollow portion, and a tip end opening portion of the ventilation passage is formed in the head portion.

(11) A syringe as set forth in the above paragraph (10), wherein the filter is provided at the tip end opening portion of the ventilation passage.

(12) A syringe as set forth in the above paragraph (10) or (11), wherein when the pusher is moved in the longitudinal direction thereof, air is distributed between the space and the ventilation passage through a gap between the head portion and the gasket.

In the present invention as set forth in the above paragraphs (1) to (12), preferable examples further include the following modes.

(13) A syringe as set forth in any of the above paragraphs (1) to (12), wherein the connection between the gasket and the pusher is performed by screw engagement.

(14) A syringe as set forth in any of the above paragraphs (1) to (13), wherein at least a portion, making contact with the pusher, of the sealing member is formed of an elastic material.

(15) A syringe as set forth in any of the above paragraphs (1) to (14), wherein a portion, making contact with the pusher, of the sealing member is comprised of at least one ring-shaped projected portion projected from the inside surface of the insertion hole toward a central portion.

(16) A syringe as set forth in any of the above paragraphs (1) to (15), wherein the outer tube is provided at a base end portion thereof with an outer tube flange including fixing means (locking portion) for fixing the sealing member.

(17) A syringe as set forth in any of the above paragraphs (1) to (15), including a plate-like outer tube flange formed integrally with the sealing member and formed separately from the outer tube.

(18) A syringe as set forth in the above paragraph (17), wherein the sealing member is formed of an elastic material, the outer tube flange is formed of a hard material, and both of them are integrally formed by two-color molding.

(19) A syringe as set forth in any of the above paragraphs (1) to (18), wherein the pusher is variable in length.

(20) A syringe as set forth in the above paragraph (19), including maintaining means for maintaining the condition where the length of the pusher is large.

(21) A syringe as set forth in the above paragraphs (19) or (20), wherein the pusher includes, in addition to a main body portion, an operating portion which is formed separately from the main body portion and which is located on the base end side of the main body portion so as to be movable in the longitudinal direction of the pusher.

(22) A syringe as set forth in the above paragraph (21), wherein in the condition where the length of the pusher is small, a tip end portion of the operating portion abuts on the sealing member or a base end portion of the outer tube, whereby the gasket is prevented from being pushed to a tip end portion of a barrel portion of the outer tube, but in the condition where the length of the pusher is large, the gasket can be pushed to the tip end portion of the barrel portion of the outer tube.

In the present invention, the syringe structure in which the gasket is prevented from being moved to the tip end direction even if the pusher is pushed when not in use, i.e., the second-named invention is shown by the modes of the paragraphs (19) to (22) combined with the first-named invention, and provides the modes shown by the following paragraphs (23) to (26), preferably, further, the mode shown by the following paragraph (27).

(23) A syringe comprising: an outer tube provided on the tip end side thereof with a mouth portion permitting a liquid to come in and out therethrough; a gasket slidably disposed in the outer tube and partitioning the space in the outer tube into the tip end side and the base end side; and a pusher connected to the gasket and operated to move the gasket in the longitudinal direction of the outer tube, wherein the pusher includes a pusher main body, and a pusher operating portion disposed on the base end side of the pusher main body so as to be movable in the longitudinal direction of the pusher, the pusher operating portion has an abutment portion abutting on a base end portion, or a portion near the base end portion, of the outer tube in the condition where the length of the pusher is small, and in the condition where the length of the pusher is small, the abutment portion abuts on said the end portion, or the portion near the base end portion, of the outer tube, whereby the gasket is prevented from being pushed to a tip end portion of a barrel portion of the outer tube, but in the condition where the length of the pusher is large, the gasket can be pushed to the tip end portion of the barrel portion of the outer tube.

(24) A syringe as set forth in the above paragraph (23), including maintaining means for maintaining the condition where the length of the pusher is large.

(25) A syringe as set forth in the above paragraph (24), wherein either one of the pusher main body and the pusher operating portion includes an elastic piece, and a projected portion formed on the opposite side of the base of the elastic piece, while the other of the pusher main body and the pusher operating portion has a recessed portion into which the projected portion can be inserted, and in the condition where the length of the pusher is large, the projected portion is inserted into and engaged with the recessed portion by the elasticity of the elastic piece, whereby the condition where the length of the pusher is large is maintained.

(26) A syringe as set forth in any of the above paragraphs (23) to (25), wherein the outer tube is provided at a base end portion thereof with a plate-like outer tube flange, and the abutment portion abuts on a base end face of the outer tube flange in the condition where the length of the pusher is small.

(27) A syringe as set forth in the above paragraph (25), wherein a guide surface for guiding the projected portion into the recessed portion is provided in the vicinity of the recessed portion, and when the pusher operating portion is gradually moved to the base end direction relative to the pusher main body, the projected portion is slid along the guide surface, to be inserted into the recessed portion.

In each of the syringes of the above paragraphs (1) to (27), the mouth portion is ordinarily sealed with an unsealable membrane. The membrane is unsealed by puncturing with a needle body.

In the present invention, as a particularly preferable mode of each of the syringes having the above-mentioned structures, there is provided a prefilled syringe including a chemical preliminarily contained in a space (first space) surrounded by the outer tube and the gasket and located on the tip end side of the gasket.

Where the syringe has a basic structure as shown by the above paragraphs (1) to (9), the syringe is preferably a prefilled syringe containing a liquid chemical as a chemical.

BRIEF DESCRIPTION OF DRAWINGS

FIG. 6(*a*) is a partial vertical sectional view showing a second embodiment (assembled state) of the prefilled syringe according to the present invention (first-named invention), and (*b*) is a cross sectional view of a pusher main body portion along line b—b of (*a*)

FIG. 7(*a*) is a partial vertical sectional view showing a third embodiment (assembled state) of the prefilled syringe according to the present invention (first-named invention), and (*b*) is a cross sectional view of a pusher main body portion along line b—b of (*a*).

BEST MODE FOR CARRYING OUT THE INVENTION

Figure 1:
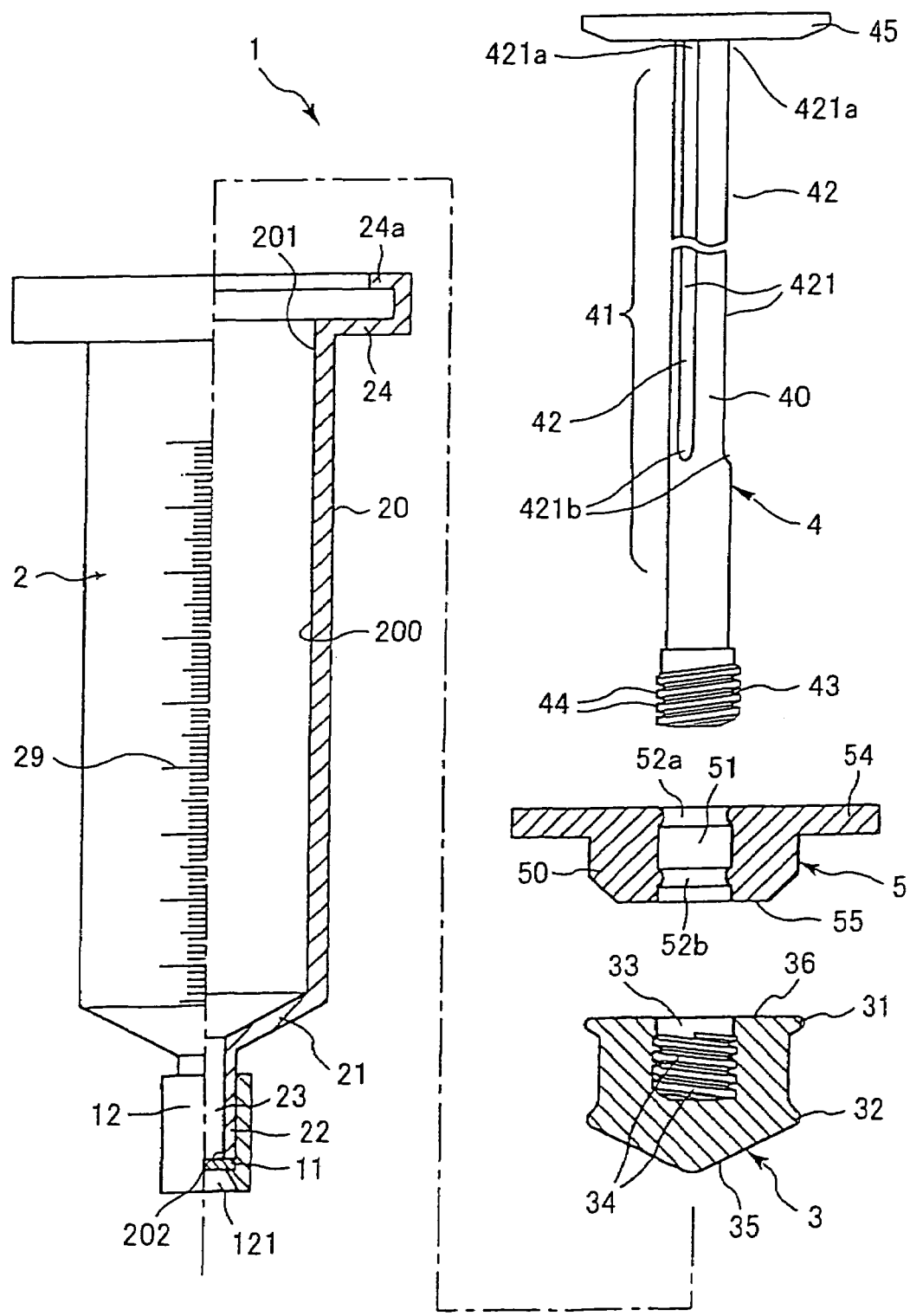
FIG. 1 is a partial vertical sectional view showing a first embodiment (disassembled state) of a syringe according to the present invention (first-named invention).

Now, the present invention will be described below, referring to the drawings.

First, the outline of syringe component members used in common in the present invention will be described, referring to FIG. 1 (disassembled state) and FIG. 2 (assembled state) showing a prefilled syringe which is one embodiment of the present invention. In these figures, a syringe 1 comprises a hollow cylindrical outer tube 2 having a mouth portion (reduced-diameter portion) 22 for discharging/injecting a liquid through a tip end opening 202, a gasket 3 disposed in the outer tube 2 and partitioning the space inside the outer tube 2 into the tip end side (a first space 27) and the base end side (a second space 26), and a pusher 4 connected to the gasket 3 so as to be sliding the gasket 3 to the tip end/base end side in the outer tube 2.

The syringe according to the first-named invention comprises a sealing member 5 disposed at a base end opening 201 of the outer tube 2, and the pusher 4 is slidably fitted in an insertion hole 51 in the sealing member 5. The pusher 4 is provided, at least on the tip side thereof (the side of connection to the gasket 3), with a hollow cylindrical portion 40 slid in close contact with the insertion hole 51 in the sealing member 5, and has variously shaped ventilation means 42 provided along the axial direction thereof. By a forward movement (pushing) of such a pusher 4, a gap generated between the ventilation means 42 of the pusher 4 and the sealing member 5 (the insertion hole 51) provides communication with the second space 26 in the outer tube 2, or provides communication between a ventilation passage inside the hollow pusher 4 and the second space 26, or provides communication between the ventilation passage inside the hollow pusher 4 and the second space 26 through deformation of the gasket 3, whereby the second space 26 in the outer tube 2 is communicated with the atmosphere.

Figure 3:
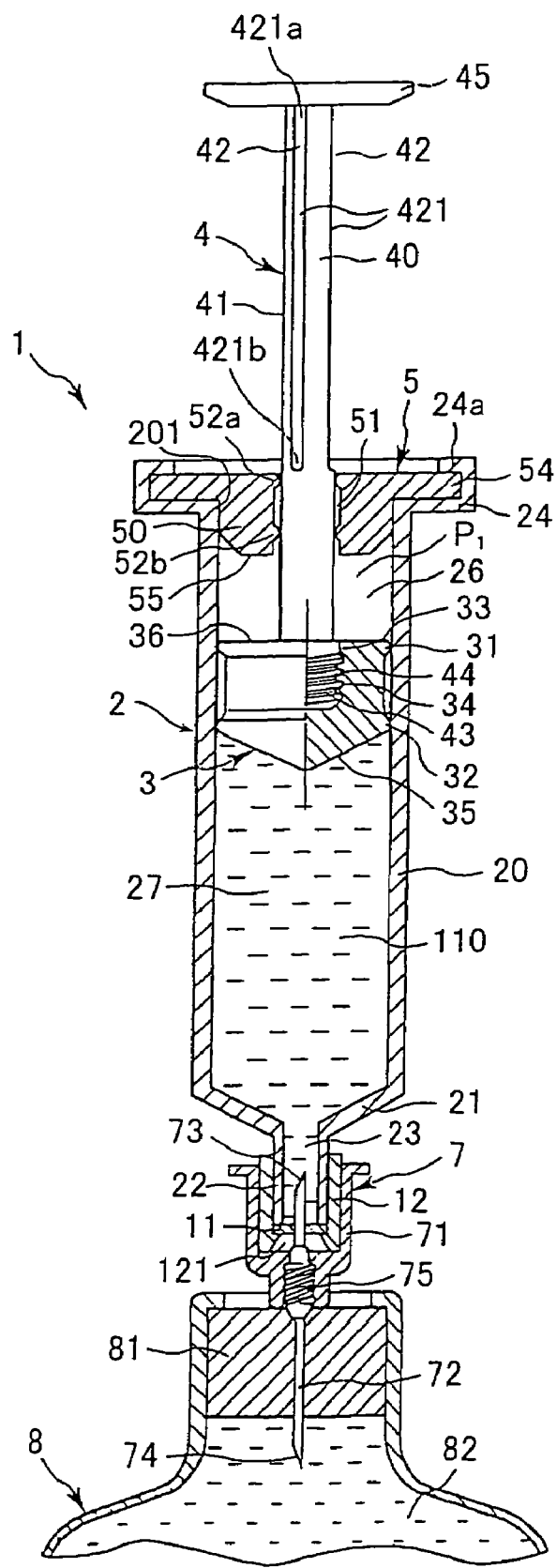
FIG. 3 is a partial vertical sectional view showing an operating condition in use of the prefilled syringe shown in FIGS. 1 and 2.
Figure 4:
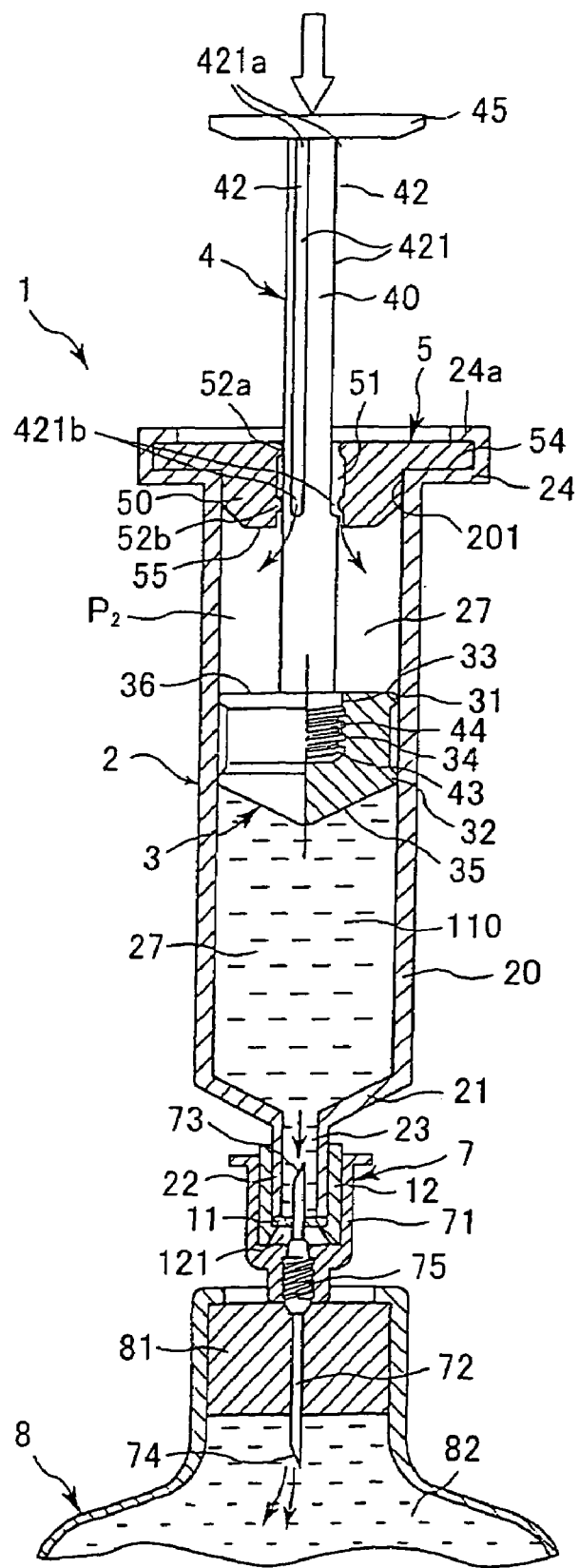
FIG. 4 is a partial vertical sectional view showing an operating condition in use of the prefilled syringe shown in FIGS. 1 and 2.
Figure 5:
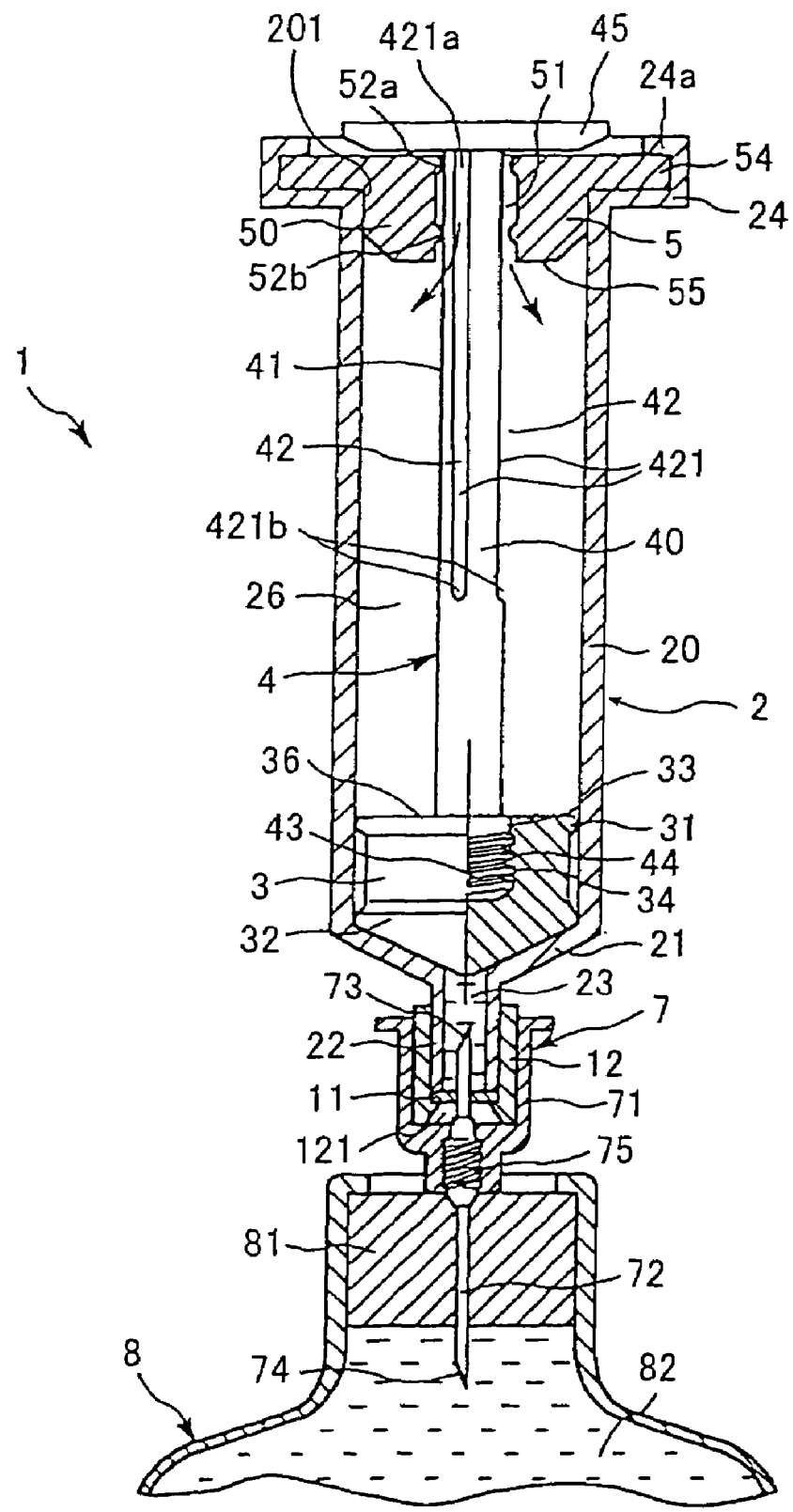
FIG. 5 is a partial vertical sectional view showing an operating condition in use of the prefilled syringe shown in FIGS. 1 and 2.

Now, the first-named invention as above will be more specifically described below, referring to some preferred embodiments. FIGS. 1 to 5 show a prefilled syringe (hereinafter sometimes referred to simply as "syringe") according to a first embodiment of the first-named invention. FIG. 1 is a partial vertical sectional view showing the disassembled state of the syringe before filling with a chemical, for illustrating syringe component members, FIG. 2(*a*) is a partial vertical sectional view of the assembled state (prefilled syringe) after filling with the chemical, and (*b*) is a cross sectional view of the pusher. FIGS. 3 to 5 are partial vertical sectional views showing operations in use of the prefilled syringe shown in FIG. 2. Incidentally, in FIGS. 1 to 5 and in FIGS. 6 to 8, which will be described later, the upper side in the figures will be referred to as the "base end" side, while the lower side will be referred to as the "tip end" side.

The syringe 1 in this embodiment comprises an outer tube (syringe outer tube) 2, a gasket 3 slidable in the outer tube 2, a pusher (plunger rod) 4 operated to move the gasket 3 in the longitudinal direction of the outer tube 2, and a sealing member 5 for sealing a base end opening 201 of a barrel portion 20 of the outer tube 2. The gasket 3 is connected to the tip end of the pusher 4.

The outer tube 2 is composed of a member of a bottomed tubular (hollow cylindrical) barrel portion 20 having a bottom portion 21 on the tip end side, and the bottom portion 21 is integrally provided at its central portion with a reduced-diameter portion 22 reduced in diameter relative to the barrel portion 20 of the outer tube 2. A tip end opening 202 of the reduced-diameter portion 22 constitutes a mouth portion through which a liquid can let in and out. The reduced-diameter portion 22 may be provided with a male screw (lure lock screw) (not shown) at the outer circumference of a base end portion thereof.

A membrane 11 formed of an elastic material, as a sealing member, is attached to the tip end opening 202 of the reduced-diameter portion 22, thereby sealing gas-tightly the lumen 23 of the reduced-diameter portion 22.

In addition, a cap 12 is fitted and fixed to the outside of the reduced-diameter portion 22. The cap 12 is used in connection with a holder 7 (which will be described later), and functions as a connection portion for connection with the holder 7. The cap 12 is provided in its tip end with an opening 121, and an outer circumferential portion of the membrane 11 is clamped between an edge portion of the opening 121 and the tip end face of the reduced-diameter portion 22, whereby the membrane 11 is fixed in a gas-tight (liquid-tight) manner. Incidentally, the reduced-diameter portion 22 and the membrane 11 and the cap 12 are preferably adhered with an adhesive or fused to each other.

The membrane 11 can be punctured with a needle body such as a double ended needle, as will be described later. In this case, the shape of the membrane 11 is not limited to the membrane-like shape inasmuch as the membrane 11 can be punctured with a needle body, and the shape may be, for example, a block-like shape (stopper body).

As the material constituting the membrane 11, for example, those materials as will be mentioned later as examples of the material constituting the gasket 3 can be used.

The outer tube 2 is integrally provided with a plate-like flange 24 on the outer circumference of the base end thereof. At the time of, for example, operating the pusher 4 to move the pusher 4 relative to the outer tube 2, the operation can be performed by putting a finger on the flange 24.

In addition, a locking portion (fixing means) 24a for fixing a sealing member 5 (which will be described later) by locking to an outer edge portion of a fixing portion 54 of the sealing member 5 is formed on the base end side of an outer circumferential portion of the flange 24. In this embodiment, the locking portion 24a is formed in an annular shape over the entire circumference of the flange 24; however, the locking portion 24a is not limited to this shape but may be a partially formed one such as, for example, a pawl member or members.

Examples of the material constituting the outer tube 2 include various resins such as polyvinyl chloride, polyethylene, polypropylene, cyclic polyolefins, polystyrene, poly-(4-methylpentene-1), polycarbonates, acrylic resins, acrylonitrile-butadiene-styrene copolymers, polyesters such as polyethylene terephthalate, polyethylene naphthalate, etc., butadiene-styrene copolymer, polyamides (for example, nylon 6, nylon 6.6, nylon 6.10, nylon 12), polysulfones, polyether sulfones, polyether-ether ketones, and ethylene-vinyl alcohol copolymer. Among these, preferred are such resins as polypropylene, cyclic polyolefins, polyesters, and poly-(4-methylpenene-1), in view of their easy moldability.

Incidentally, it is preferable for the material constituting the outer tube 2 to be substantially transparent, for securing visibility of the inside thereof.

Besides, the outer circumferential surface of the barrel portion 20 of the outer tube 2 is provided with graduations 29 (see FIG. 1). This makes it possible to grasp the amount of a liquid (an infusion 82, a liquid chemical 110, or the like) in the syringe 1.

The gasket 3 formed of an elastic material is contained in the outer tube 2. The gasket 3 is provided on its outer circumferential portion with a plurality of annular projected portions 31 and 32 over the entire circumference. The outside diameter of the projected portions 31, 32 in the natural state of the gasket 3 is greater than the inside diameter of the outer tube 2, so that in the condition where the gasket 3 is inserted in the outer tube 2, the outer circumferential portion of the gasket 3 is slid while being kept in close contact (press contact) with the inner circumferential surface 200 of the outer tube 2 by the elasticity of the gasket 3, whereby the gas-tightness (liquid-tightness) is maintained more securely, and a higher slidability can be contrived.

In this embodiment, the gasket 3 is provided with two projected portions 31 and 32 along the longitudinal direction thereof. Specifically, the projected portions 31 and 32 are provided respectively on the side of the base end face 36 and on the side of the tip end face 35 of the gasket 3. Of these projected portions 31 and 32, the projected portion 32 on the gasket tip end side is preferably provided on its base end side with a tapered surface whose outside diameter is gradually increased as the tip end thereof is approached.

Incidentally, in the present invention, the positions, the number, the sectional shapes and the like of the projected portions 31 and 32 are not limited to the above-mentioned ones.

In addition, the gasket 3 is provided with a hollow portion 33 opening to the base end face 36 thereof. A head portion of the pusher 4 (which will be described later) is inserted (screw-engaged) in the hollow portion 33. The inside surface of the hollow portion 33 is provided with a female screw 34.

The material constituting the gasket 3 is not particularly limited. Examples of the material include elastic materials such as various rubber materials such as natural rubber, butyl rubber, isoprene rubber, butadiene rubber, styrene-butadiene rubber, silicone rubbers, etc., various thermoplastic elastomers such as polyurethane-based, polyester-based, polyamide-based, polyolefin-based, and polystyrene-based elastomers, etc., and mixtures thereof.

Incidentally, it suffices that at least an outer circumferential portion of the gasket 3 is formed of the above-mentioned elastic material; for example, the gasket 3 may have a configuration in which a core portion (not shown) is formed of a resin material and an elastic material is so arranged as to cover the outer circumference of the core portion. In this case, the core portion is provided with the female screw 34.

The pusher 4 operated to move the gasket 3 in the longitudinal direction of the outer tube 2 is connected (attached) to the gasket 3.

The pusher 4 is a rod-like, preferably a round rod-like, main body portion 40, and a flange-like (plate-like) finger receiving portion 45 is provided at the base end of the main body portion 40. By pushing the finger receiving portion 45 by a finger or the like, the pusher 4 is operated to move to the tip end direction.

The main body portion 40 has a sliding portion 41 of which a maximum outer circumferential surface of a roughly hollow cylinder slides while making close contact with projected portions 52a and 52b of the sealing member 5 which will be described later. The sliding portion 41 has a solid round rod-like shape (or a hollow round rod-like shape) which is circular in cross section.

In addition, the sliding portion 41 of the main body portion 40 is provided with grooves (ventilation passages) 421 as ventilation means 42 for permitting ventilation between the exterior of the syringe 1 and the second space 26 which will be described later. The grooves 421 extend along the longitudinal direction of the main body portion 40, and open to the outer circumferential surface of the pusher 4. In this embodiment, three grooves 421 are arranged along the circumferential direction of the main body portion 40. The cross-sectional shape of the grooves 421 may be any shape, for example, U shape, V shape, angular U shape, or the like. The grooves 421 may be formed independently from each other or may be connected to each other at parts thereof.

The region where the grooves 421 are formed, in relation to the longitudinal direction of the pusher 4, is preferably determined as follows.

First, the base ends 421a of the grooves 421 are located at or in the vicinity of the base end of the main body portion 40 of the pusher 4.

Figure 2:
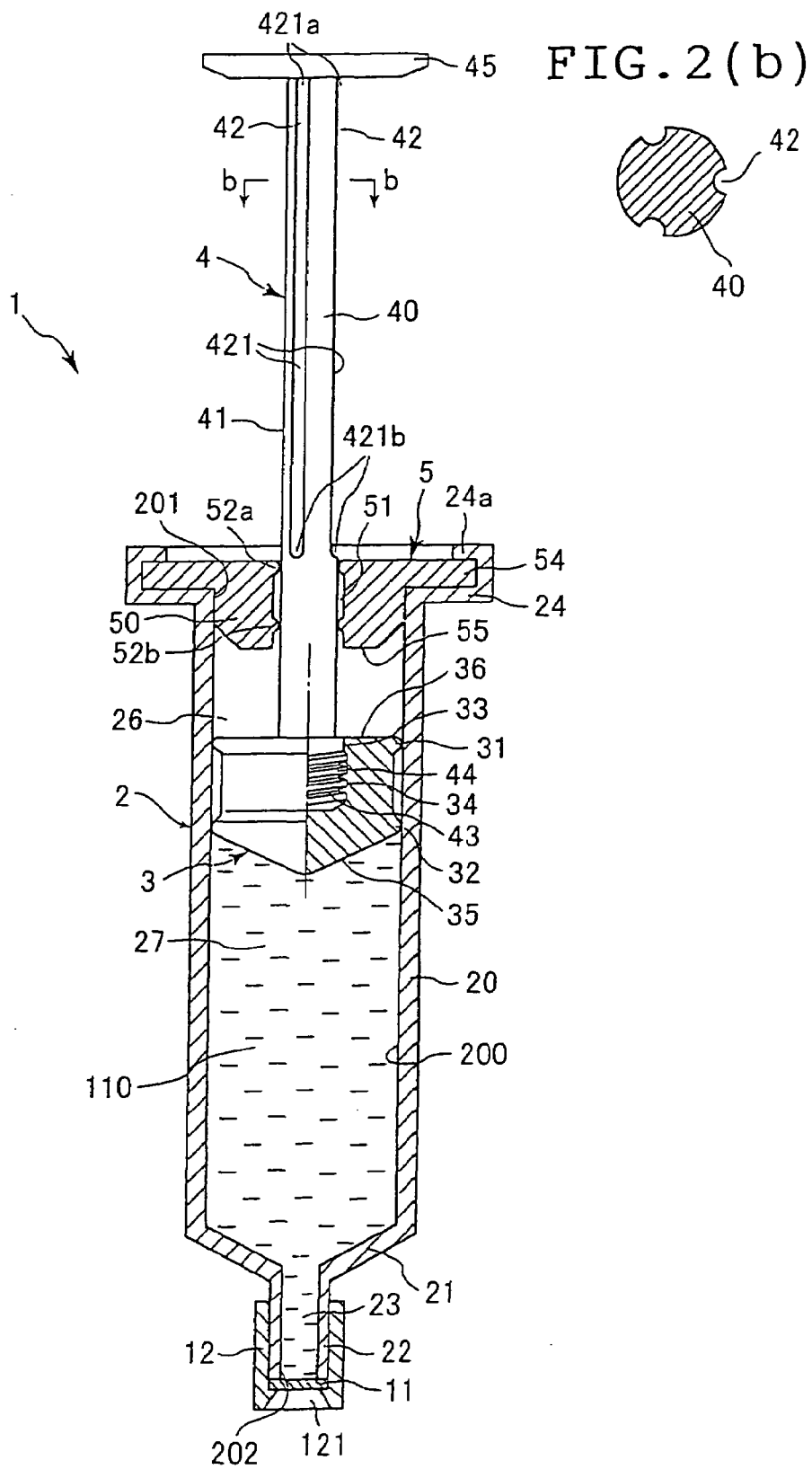
FIG. 2(*a*) is a partial vertical sectional view showing the first embodiment (prefilled syringe in assembled state) of the syringe according to the present invention (first-named invention), and (*b*) is a cross sectional view of a pusher main body portion along line b—b of (*a*).

In addition, the tip ends 421b of the grooves 421 are located on the base end side relative to the projected portion 52b of the sealing member 5 (which will be described later) in the non-used condition of the syringe 1, i.e., in the condition before the pusher 4 is pushed to the tip end direction (hereinafter referred to as "pre-operation condition"), as shown in FIG. 2. In the configuration shown in FIG. 2, the tip ends 421b of the grooves 421 are located on the base end side of and in the vicinity of the projected portion 52a of the sealing member 5. This ensures that in the condition before the pusher 4 is pushed to the tip end direction, air distribution is absent in the insertion hole 51 through the grooves 421, and the second space 26 is maintained in the state of being shut off (hermetically sealed) from the atmosphere. As a result, penetration of foreign matter such as dirt, dust or the like or penetration of bacteria into the second space 26 together with the atmospheric air is prevented, and sanitation is maintained.

Incidentally, the number and formation locations of the grooves 421, the shapes of the grooves 421, and the like are not limited to the above-mentioned ones.

A head portion (connection portion) 43 to be inserted in the hollow portion 33 of the gasket 3 and connected to the gasket 3 is provided on the tip end side of the main body portion 40.

The head portion 43 is provided at its outer circumference with a male screw 44 which can make screw engagement with the female screw 34 provided at the inside surface of the hollow portion 33 of the gasket 3. By screw engagement between the male screw 44 and the female screw 34, the gasket 3 and the pusher 4 are connected to each other (see FIG. 2).

Examples of the material constituting the pusher 4 include various reins such as polyvinyl chloride, polyethylene, polypropylene, polystyrene, poly-(4-methylpentene-1), polycarbonates, acrylic resins, acrylonitrile-butadiene-styrene copolymers, polyesters such as polyethylene terephthalate, polyethylene naphthalate, etc., butadiene-styrene copolymer, polyamides (for example, nylon 6, nylon 6.6, nylon 6.10, nylon 12), polysulfones, polyether sulfones, polyether-ether ketones, and ethylene-vinyl alcohol copolymer based resins. Among these, preferred are such resins as polypropylene, polyesters, and poly-(4-methylpentene-1), in view of their easy moldability.

Since the connection between the gasket 3 and the pusher 4 is thus achieved by the screw engagement structure (one example of play-free mechanism), the connection between them can be performed assuredly, the operation on the pusher 4 will not be attended by disengagement between the gasket 3 and the pusher 4, and the pusher 4 can easily be attached to and detached from the gasket 3.

Incidentally, in the present invention, the connection structure between the gasket 3 and the pusher 4 may be one other than the screw engagement, for example, a play-free mechanism such as firm attachment (e.g., adhesion, fusing) and fitting, or may be a played mechanism such as loose fitting.

The sealing member 5 for sealing the base end opening 201 of the outer tube 2 is attached to the base end side of the outer tube 2. The sealing member 5 is entirely formed of an elastic material, and has a roughly hollow cylindrical main body portion 50. The main body portion 50 is provided in its central portion with an insertion hole 51 for passing the main body portion 40 of the pusher 4 therethrough. In addition, a flange-like (plate-like) fixing portion 54 is formed at an outer circumferential portion of the main body portion 50 of the sealing member 5.

The insertion hole 51 is provided at its inner circumferential portion with a plurality (two) of annular projected portions 52a and 52b projected from the inside surface of the insertion hole 51 toward a central portion, over the entire circumference. With the projected portions 52a and 52b sliding while making close contact with the outer circumferential surface of the sliding portion 41 of the pusher 4, good slidability of the pusher 4 can be secured and, simultaneously, the shut-off property (gas-tightness) between the second space 26 and the atmosphere can be maintained in the pre-operation condition.

In this embodiment, two projected portions 52a and 52b are formed at a predetermined interval along the axial direction of the insertion hole 51 in the sealing member 5. This ensures that, in the pre-operation condition, the shut-off property between the second space 26 and the atmosphere can be maintained securely, and the axis deviations at the time of pushing the pusher 4 can be prevented assuredly.

Incidentally, the positions, the number, the sectional shapes, the interval, and the like of the projected portions 52a and 52b are not limited to the ones shown in the figures.

Such a sealing member 5 is so configured that the main body portion 50 is fitted in the base end opening 201 of the outer tube 2, the outer circumferential surface of the main body portion 50 makes close contact with the inner circumferential surface 200 of the outer tube 2, and an outer edge portion of the fixing portion 54 is clampedly fixed to the lock portion 24a, whereby the tip end face of the fixing portion 54 is kept in close contact with the base end face of the flange 24 (see FIG. 2). In addition, as has been described above, the projected portions 52a and 52b of the sealing member 5 make close contact with the sliding portion 41 of the pusher 4. As a result, in the pre-operation condition, the base end opening 201 of the outer tube 2 can be sealed up substantially gas-tight.

Besides, the sealing member 5 has the function of preventing the gasket 3 from slipping off from the outer tube 2.

With the sealing member 5 provided, the aseptic property of the inside of the outer tube 2 can be maintained at a high level, in the pre-operation condition. In addition, at the time of assembling the syringe 1, the aseptic property of the inside of the syringe 1 can be maintained even if the syringe 1 is packaged in a non-aseptic environment after mounting the pusher 4, so that the aseptic condition in the packaging step is unnecessitated, which is advantageous for production and assembly.

The material constituting the sealing member 5 is not particularly limited. Examples of the material include elastic materials such as various rubber materials such as natural rubber, butyl rubber, isoprene rubber, butadiene rubber, styrene-butadiene rubber, silicone rubber, etc., various thermoplastic elastomers such as polyurethane-based, polyester-based, polyamide-based, polyolefin-based, and polystyrene-based elastomers, and mixtures of these materials. Among these, preferred are thermoplastic polyurethane-based elastomers (for example, Elastoran ET680, a product by Takeda Verdishe Co., Ltd.) and polystyrene-based elastomers (for example, Rubberon MJ4300, a product by Mitsubishi Chemical Corp.).

As shown in FIG. 2, in the pre-operation condition of the syringe 1, the base end face 36 of the gasket 3 is preferably located at a position spaced by a certain degree of distance from the tip end face 55 of the sealing member 5. This makes it possible to secure to a certain extent the volume of the second space 26 and to start the pushing operation of the pusher 4 easily (with a comparatively small force). Then, it is possible to easily achieve a pressure difference $P_1-P_2$ which will be described later.

In this syringe 1, a liquid chemical 110 is preliminarily contained in a first space 27 which is a space surrounded by the outer tube 2 and the gasket 3 and which is located on the tip end side of the gasket 3 (see FIG. 2).

Specific examples of the liquid chemical 110 include vitamin agents (multi vitamin), various amino acids, anti-thrombotic such as haparin, etc., insulin, antibiotic, antineoplastic agent, analgesic, cardiac, intravenous injection anesthetic, agents against Parkinson's disease, ulcer treating agents, adrenocortial hormone, antiarrhythmic agent, and compensating electrolytes. Incidentally, in the present invention, the liquid chemical 110 is not limited to the just-mentioned ones.

Incidentally, a solid chemical such as powdery (granular) ones and freeze-dried ones may be contained in place of the liquid chemical 110. In this case, a liquid such as an infusion is introduced into the first space 27 by, for example, once pulling the pusher 4 to the base end direction, thereby dissolving the chemical in the introduced liquid to form a liquid chemical, and the pusher 4 is pushed to the tip end direction to discharge (inject) the liquid chemical.

In the next place, one example of the method of using the syringe 1 will be described, based on FIGS. 2 to 5. The method described below is an example of the case where a holder fitted with a double ended needle is connected to the syringe 1 and a liquid chemical is mixingly injected into an infusion container.

As shown in FIG. 3, the holder 7 to be connected to the syringe 1 comprises a bottomed tubular holder main body 71, a double ended needle (needle pipe) 72 provided with sharp needle ends 73 and 74 respectively at both ends thereof, and a hub (support member) 75 for supporting the double ended needle 72. The double ended needle 72 is attached to the hub 75, and the hub 75 is attached to a central portion of a bottom portion of the holder main body 71 by screw engagement.

The infusion container 8 is, for example, bottle-like or bag-like in shape, and an infusion 82 is contained therein in a liquid-tight manner. A stopper body 81 formed of an elastic material is attached to a mouth portion of the infusion container 8. The infusion container 8 is sealed liquid-tight by the stopper body 81.

The stopper body 81 can be punctured with a needle pipe such as the double ended needle 72 and other bottle needles, and when the needle pipe is pulled out, a puncture hole is closed by self-closing property, to secure the liquid-tightness.

[1] The holder 7 and the infusion container 8 as above-mentioned are prepared, and a needle end 74 of the holder 7 is first made to puncture the stopper body 81 of the infusion container 8 (see FIG. 3).

Next, the holder main body 71 of the holder 7 is fitted (put) onto the cap 12. By this, a needle end 73 is made to puncture the membrane 11 into the lumen 23 of the reduced-diameter portion 22 (see FIG. 3). In this condition, the first space 27 in the syringe 1 and the space inside the infusion container 8 are communicated to each other through the double ended needle 72.

Incidentally, the puncturing of the stopper body 81 with the needle end 74 and the puncturing of the membrane 11 with the needle end 73 may be conducted in the order reverse to the above.

[2] Subsequently, a finger is put on the finger receiving portion 45 of the pusher 4, and the pusher 4 is pushed in the tip end direction (the direction indicated by an arrow in FIG. 4). This causes the gasket 3 connected to the pusher 4 to slide inside the outer tube 2 to the tip end direction (see FIG. 4). In this instance, the sliding portion 41 of the pusher 4 moves with its outer circumferential surface sliding on the projected portions 52a and 52b of the sealing member 5.

Attendant on this movement of the gasket 3 to the tip end direction, the liquid chemical 110 in the first space 27 is discharged through the double ended needle 72, to be mixingly injected into an infusion 82 in the infusion container 82 (see FIG. 4).

Immediately after the pushing operation of the pusher 4 is started, the tip ends 421b of the grooves 421 formed in the pusher 4 are located in the vicinity of the projected portion 52a of the sealing member 5, and, at this time, the second space 26 is still maintained in the state of being shut off (hermetically sealed) from the atmosphere (see FIG. 3). When the pusher 4 and the gasket 3 are gradually moved to the tip end direction, the volume of the second space 26 located between the gasket 3 and the sealing member 5 is gradually increased, and the pressure in the second space 26 is gradually reduced. Namely, the pressure inside the second space 26 is brought to a negative pressure (a pressure lower than the atmospheric pressure). Then, at the moment when the tip ends 421b of the grooves 421 are moved beyond the projected portion 52b of the sealing member 5, the atmospheric air flows through the grooves 421 into the second space 26 kept at the negative pressure (see FIG. 4). This returns the second space 26 to the atmospheric pressure.

Here, let the pressure inside the second space 26 in the pre-operation condition be $P_1$ [atm], and let the pressure inside the second space 26 after the pushing operation of the pusher 4 to the tip end direction is started and immediately before the atmospheric air flows into the second space 26 (namely, in this embodiment, when the tip ends 421b of the grooves 421 are located at the projected portion 52b) be $P_2$ [atm], then the pressure difference $P_1-P_2$ between the two pressures is preferably not more than 0.9 atm, and more preferably in the range of 0.1 to 0.7 atm. If the pressure difference is too large, a large pushing force is needed on the pusher 4 in the beginning stage of the pushing operation of the pusher 4, so that a sufficient enhancement of the operability in the beginning stage may be not achieved.

Incidentally, the pressure $P_1$ may be equal to the atmospheric pressure, or may be higher than the atmospheric pressure (the second space 26 is preliminarily pressurized). In the latter case, the pushing operation of the pusher 4 in the beginning stage can be performed easily (with a small force).

In addition, the moving distance of the pusher 4 from the time when the pushing operation of the pusher 4 to the tip end direction is started until the time when the flow of the atmospheric air into the second space is started (in this embodiment, from the pre-operation condition until the time when the tip ends 421b of the grooves 421 have passed beyond the projected portion 52b) is preferably in the range of 2 to 10 mm, more preferably 2 to 5 mm. If the distance is too short, the shut-off condition between the second space 26 and the atmosphere may be canceled when the pusher 4 is pushed to the tip end direction by mistake when the syringe 1 is not in use; on the other hand, if the distance is too long, a large pushing force is needed on the pusher 4 in the beginning stage of the pushing operation of the pusher 4, so that a sufficient enhancement of the operability in the beginning stage may be not achieved.

[3] The pusher 4 is pushed further to the tip end direction. By this, the liquid chemical 110 in the first space 27 is gradually mixingly injected into the infusion 82 in the infusion container 8 through the double ended needle 72. The movement of the pusher 4 by pushing is performed until the tip end face 35 of the gasket 3 comes into contact with (or comes close to) the bottom portion 21 of the outer tube 2 (see FIG. 5). This makes it possible to minimize the amount of the liquid chemical 110 left in the syringe 1, and to mix (inject) the liquid chemical 110 into the infusion 82 wastelessly.

Attendant on the movement of the gasket 3 to the tip end direction by pushing the pusher 4, the volume of the second space 26 is also increased gradually; in this case, the atmospheric air flows into the second space 26 through the grooves 421 (see FIG. 5), and the second space 26 is maintained at the atmospheric pressure. This prevents the pusher 4 from returning to the base end direction, even if the hand is released from the pusher 4.

[4] In the case of further mixing a chemical composed of other components into the infusion container 8, the syringe 1 is detached from the holder 7 while keeping the needle end 74 of the double ended needle 72 puncturing the stopper body 81, then a similar syringe 1 containing the chemical to be newly mixed is set into the holder 7 in the same manner as in the step [1], and the same operations as in the steps [2] and [3] are performed. Thus, in the case of mixing a plurality of kinds of chemicals composed of different components, it suffices to prepare a plurality of syringes 1 charged with the respective chemicals and to replace the syringes 1 appropriately, so that the operation is extremely easy to carry out, and the time required for the mixing is short. In addition, the order of mixing can be arbitrarily selected. Further, in such mixing of chemicals, the chance of contact with the outside air is extremely small, and there is no possibility of bacterial pollution or mixing-in of foreign matter.

Now, some other preferred embodiments of the first-named invention will be described.

FIG. 6(a) is a vertical sectional view showing a second embodiment of the prefilled syringe according to the first-named invention, and (b) is a cross sectional view of a main body portion 40 of a pusher 4 along line b—b of (a). The following description of the second embodiment is based on the differences from the first embodiments, while omitting the description of the same items as those in the first embodiments.

The syringe 1 according to the second embodiment is the same as in the first embodiment, except for the configuration of the ventilation means. The ventilation means 42 in the syringe 1 according to the second embodiment is composed of a slit (ventilation passage) 422 formed in a main body portion 40 of a pusher 4. The slit 422 extends along the longitudinal direction of the main body portion 40, and opens to the outer circumferential surface of the main body portion 40.

The preferable region where the slit 422 is formed in relation to the longitudinal direction of the pusher 4, i.e., the positions of the base end 422a and the tip end 422b of the slit 422 are the same as those of the grooves 421 described above in the first embodiment.

FIG. 7(a) is a vertical sectional view showing a third embodiment of the prefilled syringe according to the first-named invention, and (b) is a cross sectional view of a main body portion 40 of a pusher 4 along line b—b of (a). The following description of the third embodiment will be centered on the differences from the first embodiment, while omitting the description of the same items as those in the first embodiment.

The syringe 1 according to the third embodiment is the same as in the first embodiment, except for the configuration of the ventilation means. The ventilation means 42 in the syringe 1 according to the third embodiment is composed of a lumen (ventilation passage) 423 formed in the main body portion 40 of the pusher 4 along the longitudinal direction, and a side hole 424 provided at the tip end of the lumen 423 and opening to the outer circumferential surface of the main body portion 40.

The position where the side hole 424 is formed is located between the projected portion 52a and the projected portion 52b of the sealing member 5, in the pre-operation condition. Incidentally, the position where the side hole 424 is formed may be the same as the position of the tip ends 421b of the grooves 421 in the first embodiment.

In addition, the base end of the lumen 423 is bored through the finger receiving portion 45, to be opened to the base end face of the finger receiving portion 45. A filter 9 is disposed in the vicinity of the base end of the lumen 423 in the manner of plugging up the ventilation passage of the lumen 423.

In this syringe 1, when the pusher 4 is pushed to the tip end direction and the side hole 424 passesd beyond the projected portion 52b into the second space 26 in the step [2] of the above-mentioned method of using the syringe, the atmospheric air passes through the filter 9 and then sequentially through the lumen 423 and the side hole 424, to be introduced into the second space 26.

Examples of the filter 9 include those through which air can pass but foreign matter such as dirt and dust cannot pass, and those through which air can pass but liquids cannot pass.

In addition, when a filter through which air can pass but foreign matter such as dirt and dust cannot pass and bacteria cannot pass (bacteria-impermeable filter) is used as the filter 9, penetration of bacteria into the lumen 423 can be inhibited, which is preferable.

Examples of the filter 9 include those composed respectively of a porous sintered body such as a sintered body of polyolefin, a hydrophobic non-woven fabric, a hydrophobic membrane filter, or the like.

In the syringe 1 according to the third embodiment, not only in the pre-operation condition but also during injection of the liquid chemical 110 (during introduction of the outside air into the second space 26) and after completion of the injection of the liquid chemical 110, penetration of foreign matter into the second space 26 and penetration of bacteria into the second space 26 can be securely inhibited by selecting the function of the filter 9.

Therefore, the aseptic property of a first space 27 and the second space 26 can be maintained even in the case where, for example, the pusher 4 and the gasket 3 are reciprocated (for example, where each of the suction of a liquid into the first space 27 and the discharge of the liquid from the first space 27 is conducted at least once).

Incidentally, the position where the filter 9 is disposed is not limited to the position shown in FIG. 7 but may be at an intermediate portion of the lumen 423 or in the vicinity of the side hole 424. Besides, such a filter 9 may be omitted.

Figures 8A, 8B:
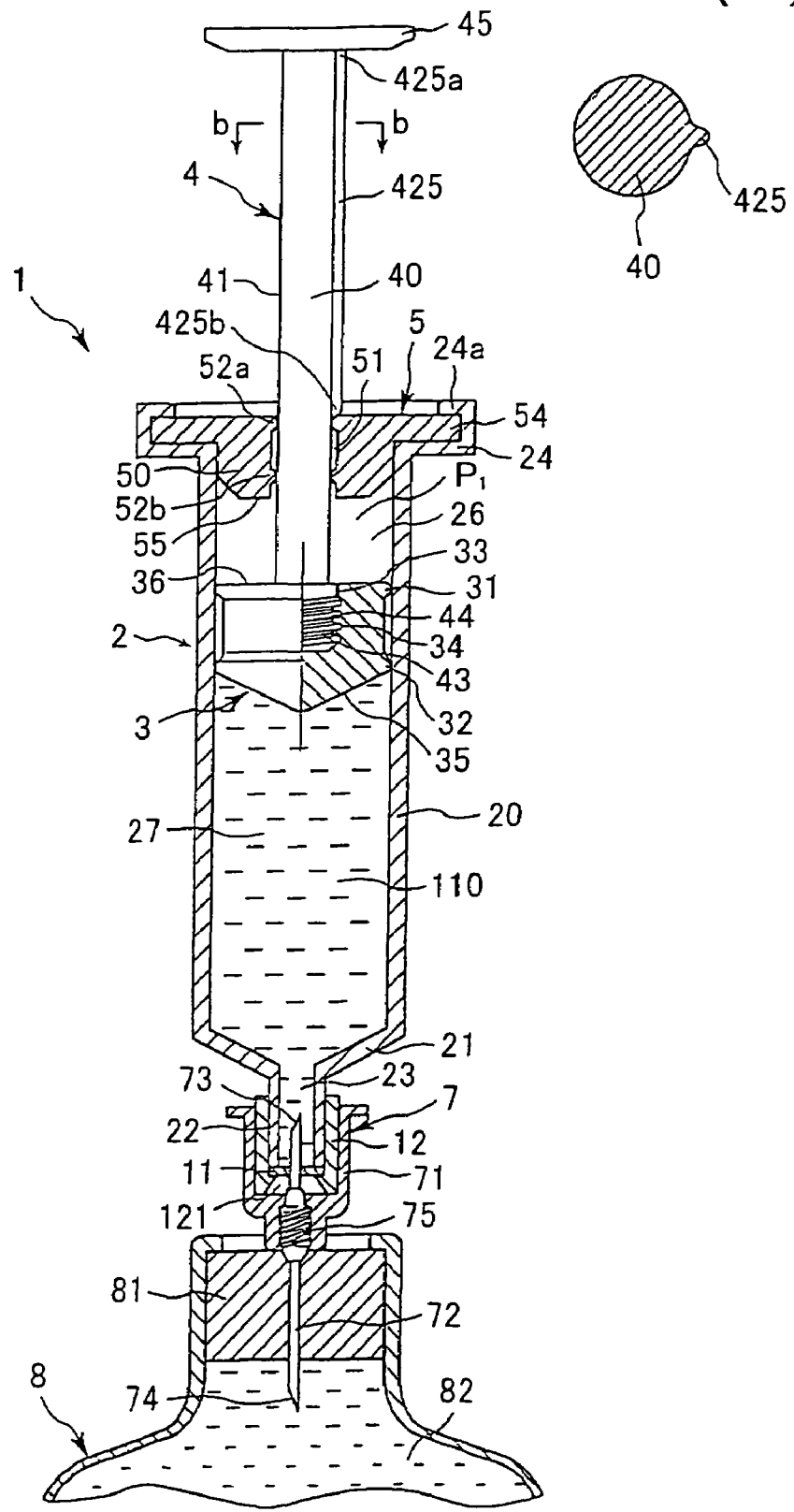
FIG. 8(*a*) is a partial vertical sectional view showing a fourth embodiment (assembled state) of the prefilled syringe according to the present invention (first-named invention), and (*b*) is a cross sectional view of a pusher main body along line b—b of (*a*).

FIG. 8(a) is a vertical sectional view showing a fourth embodiment of the prefilled syringe according to the first-named invention, and (b) is a cross sectional view of a main body portion 40 of a pusher along line b—b of (a). The following description of the fourth embodiment will be centered on the differences from the first embodiment, while omitting the description of the same items as those in the first embodiment.

The syringe 1 according to the fourth embodiment is the same as in the first embodiment, except for the configuration of the ventilation means. The ventilation means in the syringe 1 according to the fourth embodiment is composed of a convex rib 425 (rib) formed on the outer circumferential surface of the main body portion 40 of the pusher 4. The rib 425 extends along the longitudinal direction of the main body 40, and the cross sectional shape of the rib 425 is a mount-like shape, for example.

The preferable region where the rib 425 is formed in relation to the longitudinal direction of the pusher 4, i.e., the positions of the base end 425a and the tip end 425b of the rib 425 are the same as those of the grooves 421 described above in the first embodiment.

In this syringe 1, when the pusher 4 is pushed to the tip end direction in the step [2] of the above-mentioned method of using the syringe, the tip end 425b of the rib 425 first partially push out the projected portion 52a to form a gap in the vicinity of the base of the rib 425, subsequently, the tip end 425b of the rib 425 partially push out the projected portion 52b to form a gap in the vicinity of the base of the rib 425 whereby the outside air is permitted to flow into the second space 26 (which has been kept at a negative pressure) through the gaps at the projected portions 52a and 52b.

Incidentally, while only one rib 425 is provided in the configuration shown in the figures, two or more ribs may be provided.

In the next place, a syringe and a prefilled syringe according to a second-named invention will be described below, referring to FIGS. 9 to 14.

Figure 9:
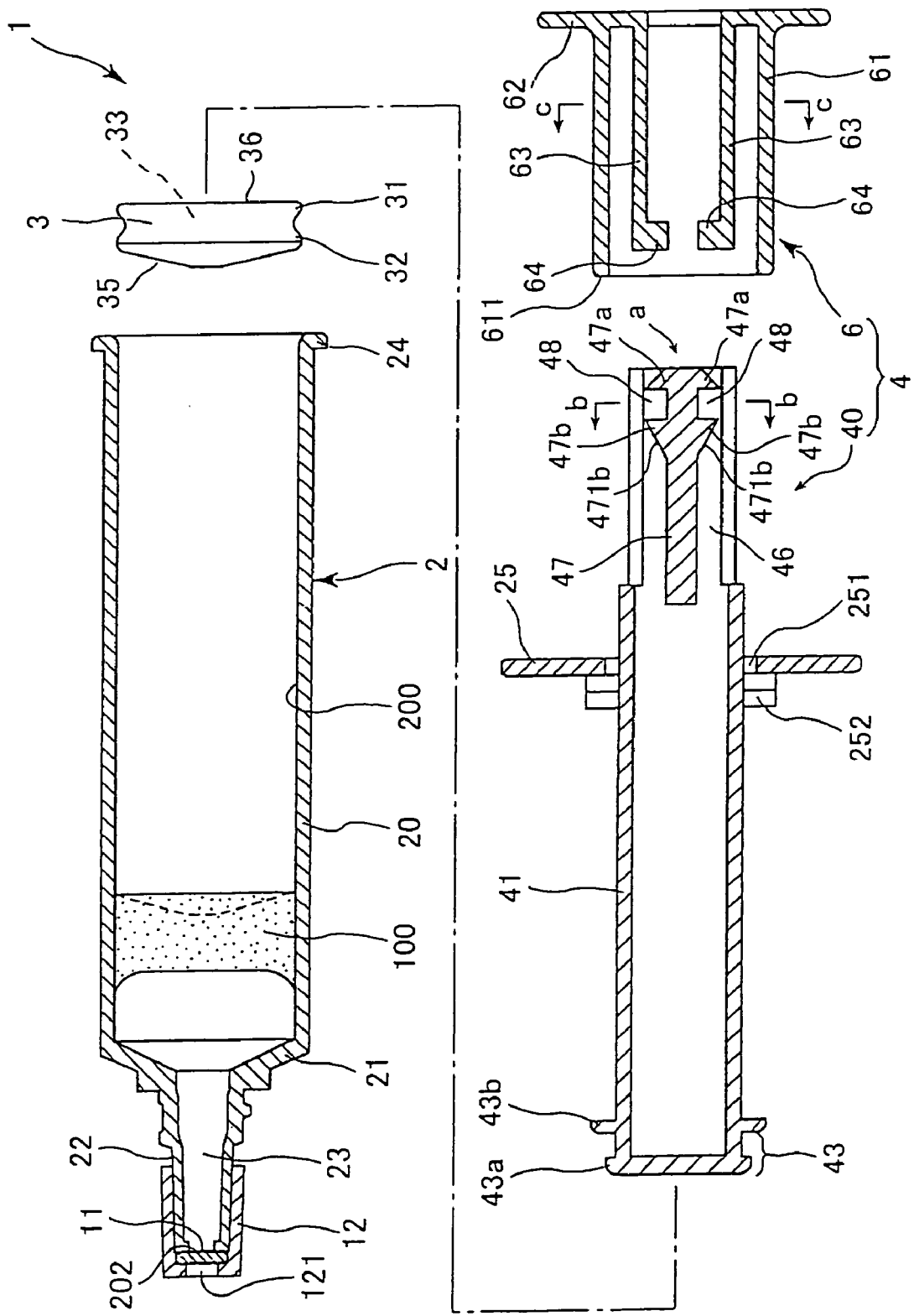
FIG. 9 is a vertical sectional view showing the disassembled state of an embodiment of a prefilled syringe according to the present invention (second-named invention).
Figure 10A:
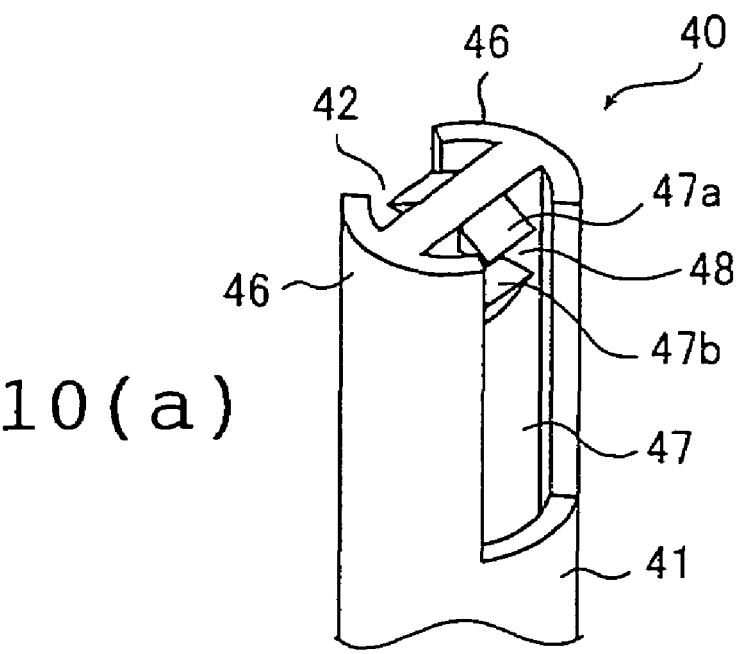
FIG. 10(*a*) is a partial perspective view of a pusher main body along arrow a of FIG. 9, (*b*) is a cross sectional view along line b—b of FIG. 9, and FIG. 10(*c*) is a cross sectional view along line c—c of FIG. 9.

FIG. 9 is a vertical sectional view showing the disassembled state of an embodiment of the syringe (prefilled syringe) according to the second-named invention, FIG. 10(a) is a partial perspective view of a pusher main body along arrow a of FIG. 9, (b) is a cross sectional view along line b—b of FIG. 9, and (c) is a cross sectional view along line c—c of FIG. 9. FIG. 11 is a vertical sectional view showing the assembled state (the state before use) of the prefilled syringe shown in FIG. 9, FIGS. 12 to 14 are vertical sectional views showing the states in use of the prefilled syringe shown in FIGS. 9 and 11, respectively. Incidentally, in FIGS. 9 to 14, the left side in the figures will be referred to as the side of the "tip end" of the syringe, and the right side will be referred to as the side of the "base end". Besides, in these figures, the same symbols as those in FIGS. 1 to 8 denote the portions which are the same as or equivalent to the above, and the description of the same items as those in the first-named invention will sometimes be omitted in the following description.

The syringe 1 according to this embodiment is a prefilled syringe in which a chemical 100 is preliminarily contained in an aseptic manner in a first space 27 in an outer tube 2, and comprises the outer tube (syringe outer tube) 2, a gasket 3 slidable in the outer tube 2, and a pusher (plunger rod) 4 operated to move the gasket 3 in the longitudinal direction of the outer tube 2.

The structure of the outer tube 2 is the same as in the first-named invention, except that a flange 24 at a base end portion is composed of a small flange and that a plate-like outer cylinder flange 25 is formed separately from a barrel portion 20. A cap 12 fitted with a membrane 11 is fitted and fixed to the tip end of a mouth portion (reduced-diameter portion) 22 of the outer tube 2.

The materials respectively constituting the outer tube 2, the membrane 11, the gasket 3 and the pusher 4 (which will be described later) are the same as those in the embodiments of the first-named invention, so that the exemplification and description thereof will be omitted.

Incidentally, it is preferable that the outer tube 2 is substantially transparent, for securing visibility of the inside thereof. In addition, the outer circumferential surface of a barrel portion 20 of the outer tube 2 is provided with graduations (not shown), to make it possible to grasp the amount of a liquid (an infusion, a liquid chemical or the like) in the syringe 1.

In this embodiment, the base end flange 24 of the barrel portion 20 of the outer tube 2 is composed of a small flange, and the plate-like outer tube flange 25 formed separately from the barrel portion 20 is attached (fixed). The outer tube flange 25 can be formed of the same material as that of the outer tube 2. The method for fixing the outer tube flange 25 to the barrel portion 20 is not particularly limited; for example, the fixation can be conducted by a method in which a pawl portion 252 (see FIG. 9) formed on the outer tube flange 25 is locked to the base end flange (small flange) 24 of the outer tube 20, and it is used in conjunction with fusing (heat fusing, high-frequency fusing, ultrasonic fusing, or the like) or adhesion (adhesion with an adhesive or a solvent). Incidentally, this configuration is not limitative, and the outer tube flange 25 may be formed integrally with the barrel portion 20.

Figure 12A:
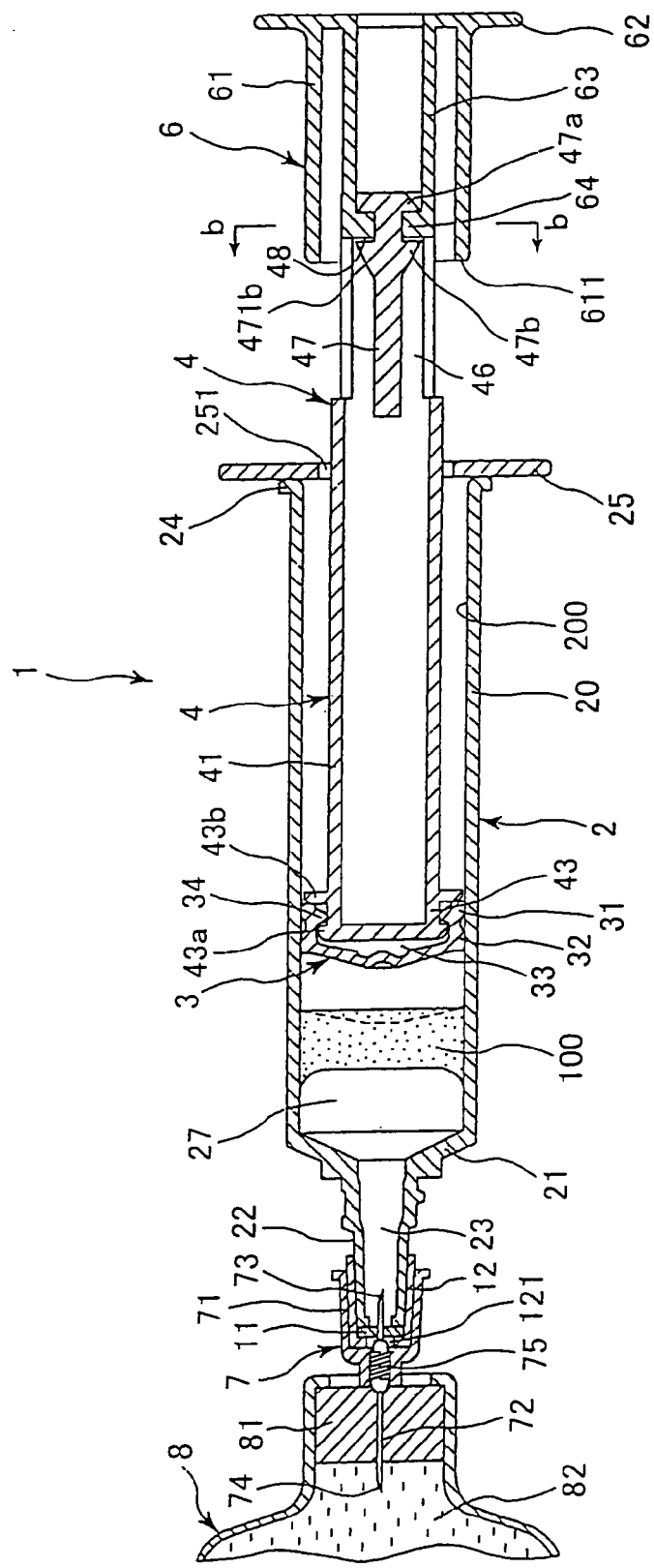
FIG. 12(*a*) is a vertical sectional view showing the condition in use of the prefilled syringe shown in FIGS. 9 and 11, and (*b*) is a cross sectional view along line b—b of (*a*).
Figure 12B:
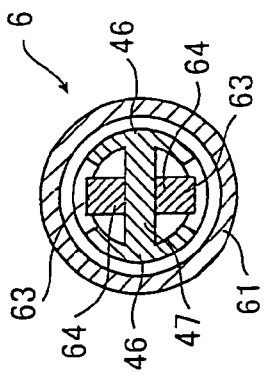

As shown in FIG. 12, at the time of operating the pusher 4 to move it relative to the outer tube 2 or in other similar situations, the operation can be performed by putting a finger on the outer tube flange 25. The outer tube flange 25 is provided in its central portion with a circular hole 251 for passing the pusher 4 therethrough.

In the configuration shown in the figures, the inside diameter of the hole 251 is smaller than the inside diameter of the barrel portion 20. This ensures that the outer tube flange 25 has also the function of preventing the gasket 3 (which will be described later) and the pusher 4 from slipping off from the outer tube 2.

The gasket 3 formed of the elastic material is contained in the barrel portion 20 of the outer tube 2. The outside diameter of the gasket 3 in the natural state is greater than the inside diameter of the barrel portion 20, and, in the condition where the gasket 3 is inserted in the barrel portion 20, the outer circumferential portion of the gasket 3 is kept in close contact (press contact) with the inner circumferential surface 200 of the barrel portion 20 by the elasticity of the gasket 3.

The gasket 3 is provided at its outer circumferential portion with a plurality of annular projected portions 31 and 32 over the entire circumference. With the projected portions 31 and 32 slid while making close contact with the inner circumferential surface 200 of the barrel portion 20, the gas-tightness (liquid-tightness) can be maintained more assuredly, and a higher slidability can be contrived.

In this embodiment, two projected portions 31 and 32 are arranged in the longitudinal direction of the gasket 3. Specifically, the projected portions 31 and 32 are provided respectively at a base end portion and a tip end portion of the gasket 3.

Incidentally, in the present invention, the positions, the number, the sectional shapes and the like of the projected portions 31 and 32 are not limited to the above-mentioned ones.

In addition, the gasket 3 is provided with a hollow portion 33 opening to the base end face thereof. A head portion 43 of the pusher 4 which will be described later is inserted (fitted) in the hollow portion 33.

As shown in FIG. 11, in the syringe 1, a chemical 100 is preliminarily contained in a space 27 surrounded by the outer tube 2 and the gasket 3 and located on the tip end side of the gasket 3.

The chemical 100 may be liquid or may be solid (solid matter, powdery, granular); in this embodiment, a solid chemical 100 is contained. The chemical 100 is obtained by freeze drying a liquid chemical injected into the syringe 1 through a reduced-diameter portion 22, and is solidified in a fixed shape to form a cake (lump) of the chemical.

Specific examples of the chemical 100 include vitamin agents (multi vitamin), various amino acids, antithrombotics such as heparin, etc., insulin, antibiotics, antineoplastic agents, analgesics, cardiac, intravenous injection anesthetic, agents against Parkinson's disease, ulcer treating agents, adrenocortical hormone, antiarrhythmic agent, compensating electrolytes, protease inhibitor, and tromboxane synthesis inhibitor. Incidentally, in the present invention, the chemical 100 naturally is not limited to the just-mentioned.

The pusher 4 operated to move the gasket 3 inside the barrel portion 20 of the outer tube 2 in the longitudinal direction is connected (attached) to the gasket 3.

In this embodiment of the second-named invention, the pusher 4 is composed of a pusher main body 40, and a pusher operating portion 6 disposed on the base end side of the pusher main body 40 so as to be movable in the longitudinal direction of the pusher 4, and the length (overall length) of the pusher 4 is variable (extendable and contractible).

Besides, in this embodiment, the pusher main body 40 has a hollow cylindrical portion 41. The hollow cylindrical portion 41 is provided at its tip end with a brim-like first flange 43a and a second flange 43b located in the vicinity of the base end side of the first flange 43a.

A hollow cylindrical portion 41 located on the tip end side of the second flange 43b and the first flange 43a constitute a head portion 43. The head portion 43 is inserted in the hollow portion 33 of the gasket 3. An engaging portion 34 projecting to the inside is formed at an inner circumferential portion near the opening of the hollow portion 33 of the gasket 3, and the engaging portion 34 is inserted between the first flange 43a and the second flange 43b. This ensures that the engaging portion 34 is engaged with the first flange 43a and the second flange 43b, whereby the gasket 3 and the pusher 4 (pusher main body 40) are linked to each other.

Incidentally, the method of linking the gasket 3 and the pusher 4 (pusher main body 40) is not limited to the configuration shown in the figure; for example, they may be linked by screw engagement, or may be attached by adhesion, fusing, or the like.

Figure 10B:
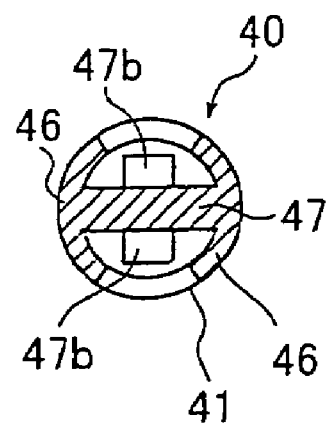
Figure 10C:
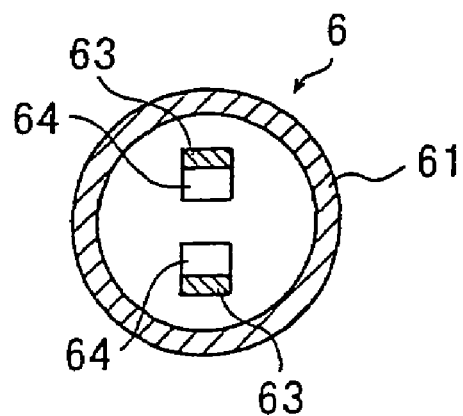
Figure 11:
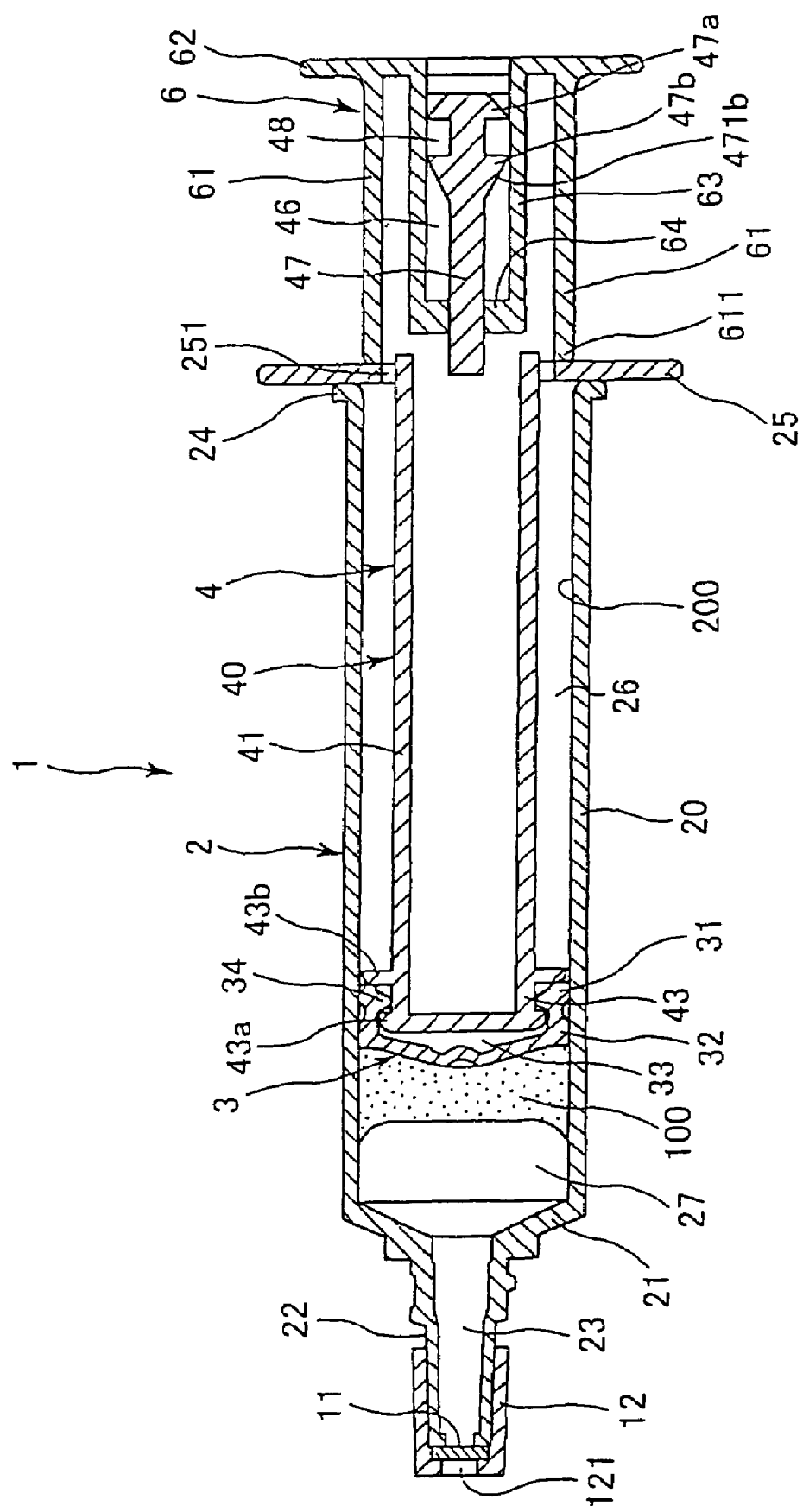
FIG. 11 is a vertical sectional view showing the assembled state (the state before use) of the prefilled syringe shown in FIG. 9.

As shown in FIGS. 9 and 10, on the base end side of the hollow cylindrical portion 41, a pair of arm portions 46 as if formed by cutting out the pipe wall on the upper and lower sides (in the figure) from the hollow cylinder similar to the hollow cylindrical portion 41 are formed projectingly toward the base end. The pair of arm portions 46 are linked by a rail portion 47 formed therebetween and extending in the longitudinal direction. The cross-sectional shapes of the pair of arm portions 46 and the rail portion 47 are such that they are roughly H-shaped as a whole.

At a base end portion of the rail portion 47, projected portions 47a roughly in the shape of a right-angled triangle in section are formed respectively at upper and lower portions in the figure. The inclined surfaces of the projected portions 47a are directed toward the base end side.

Besides, on the tip end side of the projected portions 47a, projected portions 47b roughly in the shape of a right-angled triangle in section are formed respectively at upper and lower portions in the figure, with an interval therebetween. The inclined surfaces (guide surfaces 471b) of the projected portions 47b are directed toward the tip end side. Between the projected portions 47a and the projected portions 47b, roughly tetragonal recessed portions 48 are formed so as to be defined between the projected portions 47a and the projected portions 47b. The guide surfaces 471b, which are the inclined surfaces of the projected portions 47b, display the function of guiding projected portions 64 of the pusher operating portion 6 described later into the recessed portions 48.

The pusher operating portion 6 has a hollow cylindrical portion 61 greater in inside and outside diameters than the hollow cylindrical portion 41 of the pusher main body 40. The hollow cylindrical portion 61 is provided at its base end with a flange-like (plate-like) finger receiving portion 62. In the condition where the syringe 1 is in use, the finger receiving portion 62 is pushed by a finger or the like, or the finger receiving portion 62 is pulled by hooking a finger thereon, whereby the pusher 4 is operated to move in the longitudinal direction thereof.

From the finger receiving portion 62 located on the inside of the hollow cylindrical portion 61, an upper-lower pair (in the figure) of plate-like elastic pieces (arm portions) 63, 63 are projected toward the tip end. Namely, the elastic pieces 63, 63 are located on the inside of the hollow cylindrical portion 61. The elastic pieces 63, 63 are provided at their tip end portions (on the opposite side of their bases) with roughly tetragonal projected portions 64, 64 projected toward each other (toward the inside). The projected portions 64 are corresponding in shape to the recessed portions 48.

As shown in FIG. 11, in the assembled state, the pusher 4 as above is in the condition where the rail portion 47 of the pusher main body 40 is inserted between both the projected portions 64 of the pusher operating portion 6, whereby both the members are united. The size of the gap between both the projected portions 64 is approximately equal to the width (thickness) of the rail portion 47. The pusher operating portion 6 can be moved in the longitudinal direction relative to the pusher main body 40, by the sliding of both the projected portions 64 on the rail portion 47 while clamping the rail portion 47 therebetween. Due to this movement, the length of the pusher 4 is varied (contracted and extended) between the short state shown in FIG. 11 and the long state shown in FIG. 12.

In the pre-use condition of the syringe 1 shown in FIG. 11, the pusher 4 is in the short state, while the gasket 3 is located at a position spaced by a predetermined distance in the base end direction from the bottom portion 21, and a space 27 is formed on the tip end side of the gasket 3. In addition, a tip end portion (abutment portion) 611 of the hollow cylindrical portion 61 of the pusher operating portion 6 is abutting on the base end face of the outer tube flange 25. Incidentally, the tip end portion 611 may be so configured that it can abut on a portion other than the outer tube flange 25, inasmuch as the other portion is in the vicinity of a base end portion of the outer tube 2.

In the pre-use condition as above, if the pusher operating portion 6 is pushed to the tip end direction, it is impossible to move the pusher 4 and the gasket 3 further to the tip end direction, since the tip end portion 611 of the hollow cylindrical portion 61 is abutting on the base end face of the outer tube flange 25; therefore, it is impossible to push the gasket 3 completely to the tip end portion (bottom portion 21) of the barrel portion 20 of the outer tube 2. Therefore, even when the pusher 4 (pusher operating portion 6) is pushed by some force exerted in the pre-use condition (during transportation, during storage, or the like) of the syringe 1, the gasket 3 is prevented from moving to the tip end direction. This produces the following three merits.

(1) The cake (lump) of the chemical 100 can be prevented from being collapsed under pressing by the moved gasket 3, and the beautiful appearance of the product can be securely maintained until the time of use.

(2) It is possible to prevent the chemical 100 collapsed into a powdery form due to the movement of the gasket 3 to the tip end direction (or a chemical which has been powdery from the beginning) from entering into the gap between the outer circumferential surface of the gasket 3 and the inner circumferential surface 200 of the barrel portion 20. Therefore, in the case of feeding the chemical 100 by use of the syringe 1, it is possible to securely prevent the feed amount of the chemical 100 from being deviated (reduced to below a prescribed amount) due to the remaining of the chemical 100, which has entered into the gap between the outer circumferential surface of the gasket 3 and the inner circumferential surface 200 of the barrel portion 20, without being dissolved in the liquid sucked into the outer tube 2.

(3) In the case where the chemical 100 contained in the space 27 is a liquid (liquid chemical), the pressure of the contained liquid chemical is not raised even if the pusher 4 is pushed. Therefore, even if the pusher 4 is pushed, it is possible to securely prevent the trouble that the liquid chemical leaks out of the reduced-diameter portion 22 by breaking the membrane 11 or the trouble that the liquid chemical leaks to the base end side of the gasket 3 via the gap between the outer circumferential surface of the gasket 3 and the inner circumferential surface 200 of the barrel portion 20.

In addition to the above-mentioned merits, according to the second-named invention, there is also the merit that since the length of the pusher 4 is variable, the overall length of the syringe 1 in the pre-use condition shown in FIG. 11 can be set short, and the space required during transportation and storage of the syringe 1 can be reduced.

In the syringe 1 as above, the length of the pusher 4 is enlarged at the time of use, by the following procedure.

When the pusher operating portion 6 is gradually moved to the base end direction relative to the pusher main body 40 starting from the condition shown in FIG. 11, both the projected portions 64 are slid along both the guide surfaces 471b while being so guided as to be spaced from each other, whereby, attendant on the elastic deformation of both the elastic pieces 63 so as to be opened wider, both the projected portions 64 ride over both the projected portions 47b to be inserted and fitted into both the recessed portions 48, respectively, resulting in the condition shown in FIG. 12. In the condition shown in FIG. 12, the condition where both the projected portions 64 are inserted and fitted in both the recessed portions 48 is maintained by the elasticity of both the elastic pieces 63, and, due to the engagement between both the members, the long state of the pusher 4 can be maintained (held).

Thus, in this embodiment, when the pusher operating portion is moved by pulling it to the base end direction starting from the condition shown in FIG. 11 so as to obtain the long state of the pusher 4, the pusher main body 40 and the pusher operating portion 6 are automatically locked (fixed), so that the operability is extremely good.

In addition, in this embodiment, the recessed portions 48 (projected portions 47a, 47b), the elastic pieces 63 and the projected portions 64 constitute maintaining means (lock mechanism) for maintaining the long state of the pusher 4. Incidentally, contrary to the configuration shown in the figures, the pusher main body 40 may be provided with the same members as the elastic pieces 63 and the projected portions 64, and the pusher operating portion 6 may be provided with the same members as the recessed portions 48. Besides, while the elastic pieces 63, the projected portions 64 and the recessed portions 48 are provided on both the upper and lower sides in the figures in the configuration shown in the figures, these members may be provided on only one side.

Figure 14:
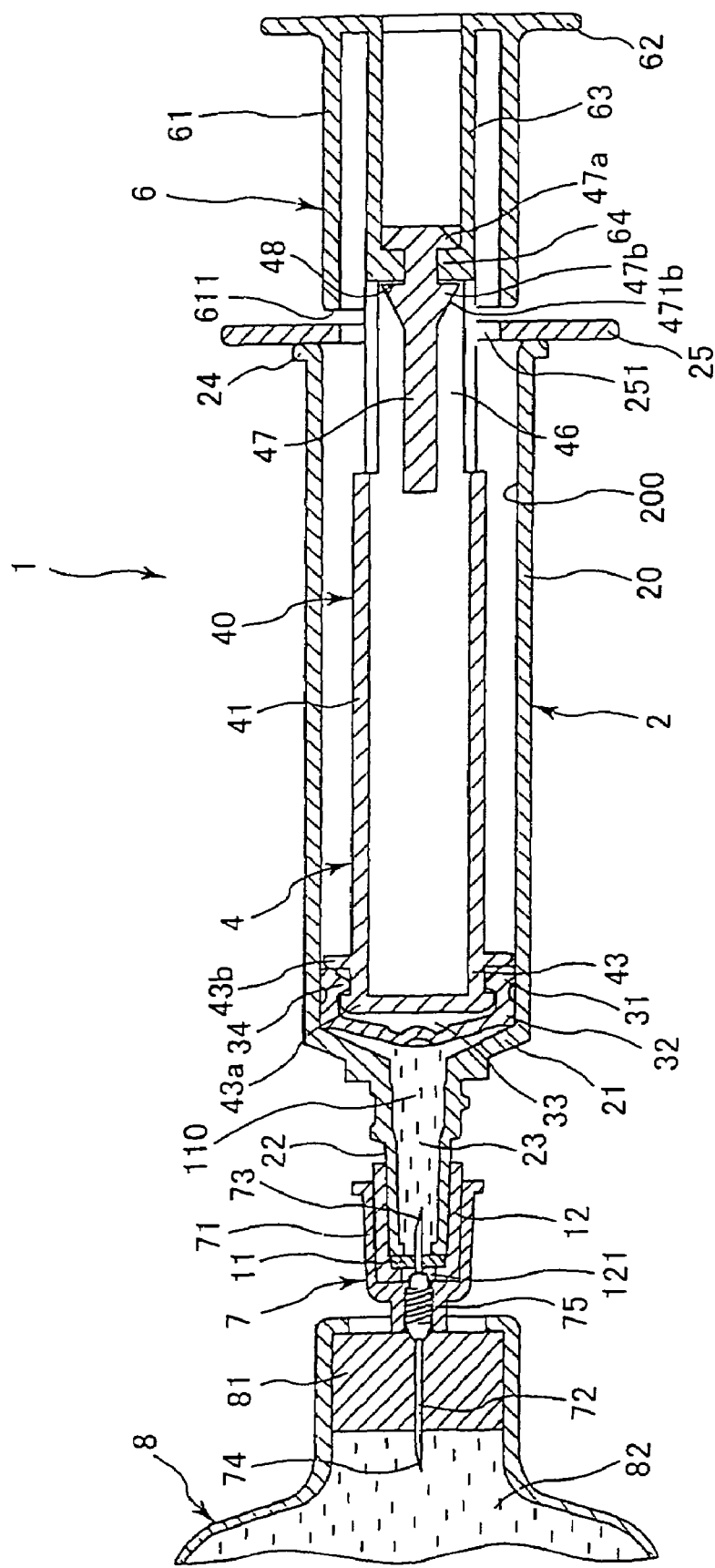
FIG. 14 is a vertical sectional view showing the condition in use of the prefilled syringe shown in FIGS. 9 and 11.

In the condition where the pusher 4 is set long, the length of the pusher 4 is sufficiently large, so that the gasket 3 can be pushed completely to the tip end portion (bottom portion 21) of the barrel portion 20 of the outer tube 2, as shown in FIG. 14. Specifically, in the condition where the pusher 4 is set long, when the tip end face of the gasket 3 makes contact with (or is located close to) the inside surface of the bottom portion 21, the tip end portion 611 of the hollow-cylindrical portion 61 does not make contact with the base end face of the outer tube flange 25.

Now, one example of the method of using the syringe 1 having the pusher 4 as above-mentioned will be described below. The method described below is one example of the case where a holder with a double ended needle is connected to a syringe 1 and a liquid chemical is mixingly injected into an infusion container.

As shown in FIG. 12, the holder 7 to be connected to the syringe 1 is composed of a bottomed tubular holder main body 71, the double ended needle (needle pipe) 72 provided at both ends thereof with sharp needle ends 73 and 74, and a hub (support member) 75 for supporting the double ended needle 72. The double ended needle 72 is attached to the hub 75, and the hub 75 is mounted to a central portion of a bottom portion of the holder main body 71 by screw engagement.

The infusion container 8 is bottle-like or bag-like in shape, and an infusion 82 is contained therein in a liquid-tight state. A stopper body 81 formed of an elastic material is mounted in a mouth portion of the infusion container 8. The infusion container 8 is sealed up in a liquid-tight manner by the stopper body 81.

The stopper body 81 can be punctured with a needle pipe such as the double ended needle 72 and other bottle needle, and when the needle pipe is pulled out, the puncture hole is closed due to the self-closing property, whereby the liquid-tightness is secured.

[1] The holder 7 and the infusion container 8 as above are prepared, and the stopper body 81 of the infusion container 8 is first punctured with the needle end 74 of the holder 7 (see FIG. 12(*a*)).

Next, the holder main body 71 of the holder 7 is fitted to (covered with) a cap 12. By this, the needle end 73 punctures a membrane 11, to enter a lumen 23 of a reduced-diameter portion 22 (see FIG. 12(*a*)). In this condition, a space 27 in the syringe 1 and the space inside the infusion container 8 are communicated with each other through the double ended needle 72.

Incidentally, the puncturing of the stopper body 81 with the needle end 74 and the puncturing of the membrane 11 with the needle end 73 may be conducted in an order reverse to the above.

Figure 13:
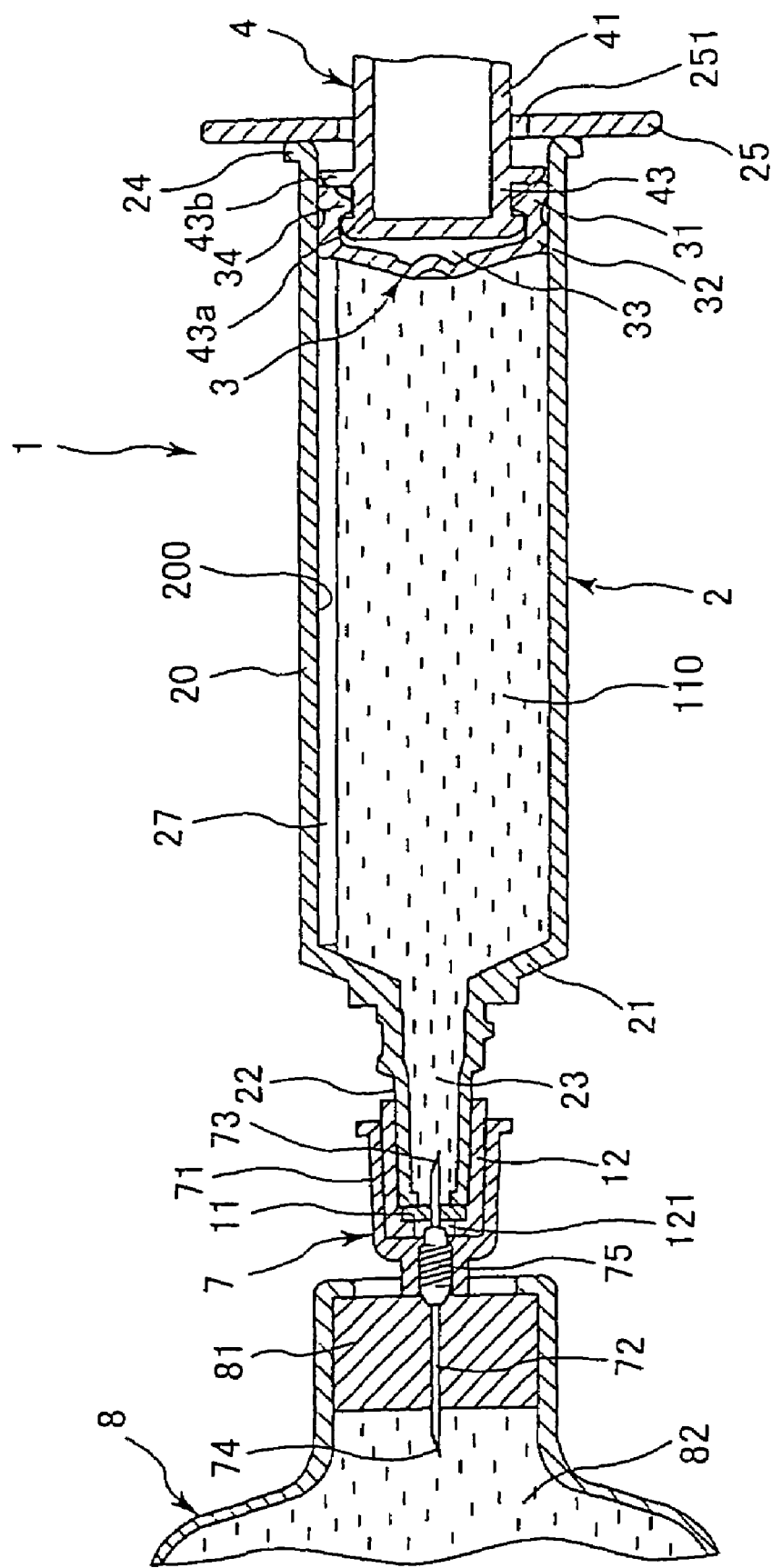
FIG. 13 is a vertical sectional view showing the condition in use of the prefilled syringe shown in FIGS. 9 and 11.

[2] Next, the pusher 4 is set to be long (see FIG. 12(*a*)), and thereafter the pusher 4 is pulled to the base end direction to slide the gasket 3 to the base end direction, whereby an infusion 82 is introduced (sucked) into the space 27 (see FIG. 13).

[3] Subsequently, a swing or vibration is applied to the syringe 1, whereby a chemical 100 is dissolved or dispersed in the infusion 82 introduced into the space 27, to form a liquid chemical 110 containing the effective components of the chemical 100 (see FIG. 13). Incidentally, examples of the liquid chemical 110 include a solution dissolved of the chemical 100, and a suspension (emulsion) containing the chemical 110. If necessary, the operation of applying a swing or vibration to the syringe 1 may be conducted after the syringe 1 is once detached from the holder 7.

[4] After the liquid chemical 110 is obtained, the pusher 4 is pushed to the tip end direction, to slide the gasket 3 to the tip end direction. As a result, the liquid chemical 110 in the space 27 is discharged via the double ended needle 72, and is mixed into the infusion 82 in the infusion container 8 (see FIG. 14). The movement of the pusher 4 by pushing it is conducted until the tip end face of the gasket 3 makes contact with (or is brought close to) the bottom portion 21 of the outer tube 2. This ensures that the amount of the liquid chemical 110 left in the syringe 1 can be minimized, and a prescribed amount of the chemical 100 can be accurately mixed.

Thus, in the case of using a prefilled syringe such as the syringe 1 in this embodiment, at the time of mixingly injecting the chemical 100 or at the time of injection, the chance of contact with the atmospheric air is extremely low, there is no possibility of bacterial pollution or mixing-in of foreign matter, the risk of infection can be reduced, there is no need for replacement of the container, and contamination of the chemical or taking one chemical for another can be prevented assuredly.

While the syringe (prefilled syringe) according to the second-named invention has been described above referring to the embodiment shown in the figures, the present invention is not limited to the embodiment, and the individual portions constituting the syringe can be replaced with those of arbitrary configurations which can display functions the same with or equivalent to the above-mentioned. Besides, arbitrary components may be added.

In the present invention, the configuration of the mouth portion at the tip end portion of the outer tube is not limited to the one shown in the figures; for example, one that does not have a membrane for sealing the mouth portion and one that is used with an injection needle attached to the mouth portion may also be adopted.

Besides, the pusher may have any structure inasmuch as the length thereof is variable; for example, a pusher having such a main body portion that plate pieces intersect each other to obtain a cross-like section may be adopted.

Further, one example of a preferred embodiment which has both the above-described first embodiment, particularly the embodiment having the hollow pusher structure comprising a filter, and the contractible/extendable pusher structure embodying the second-named invention and which attains all the first to third objects of the present invention is illustrated in FIGS. 15 to 19.

Figure 15:
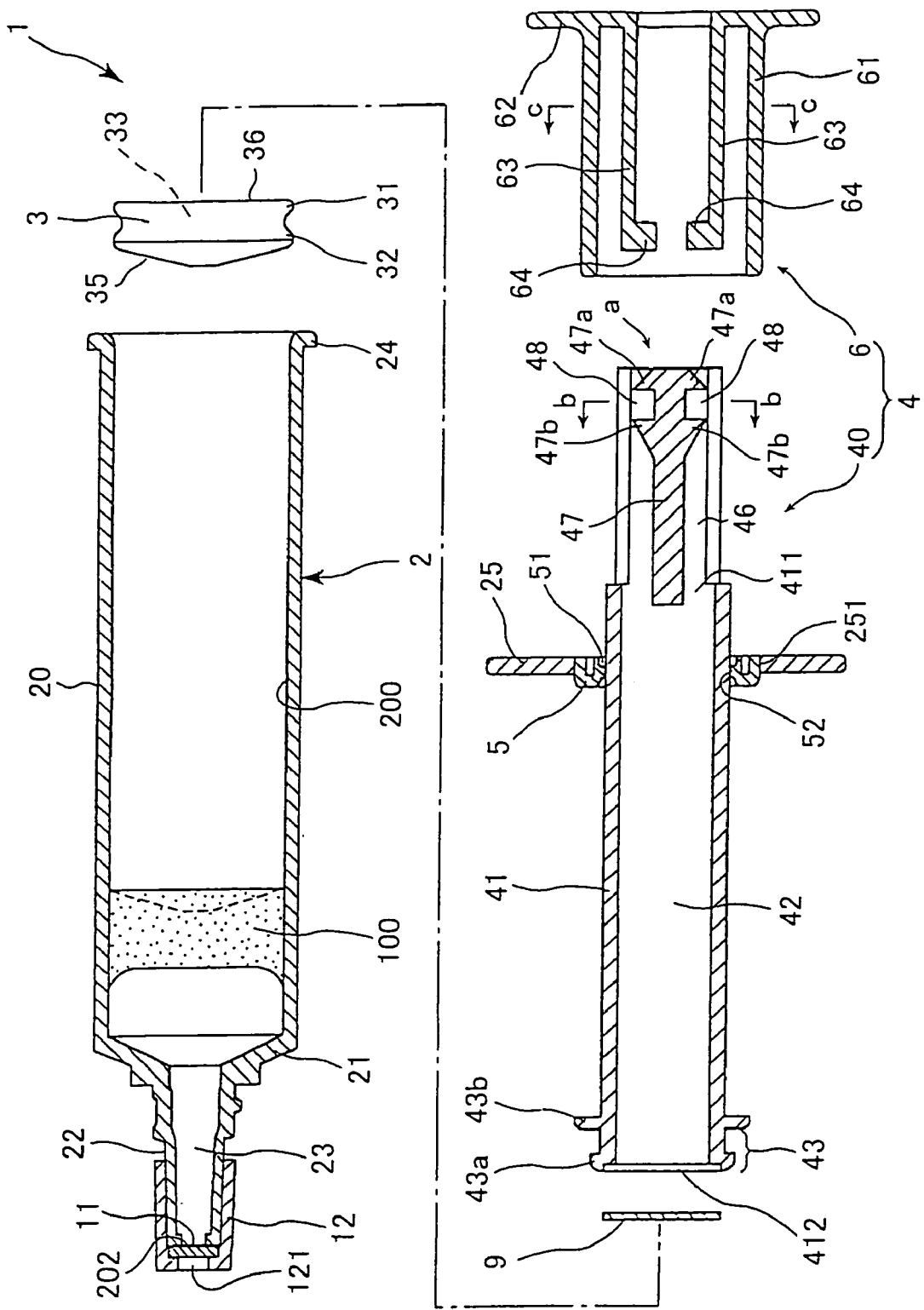
FIG. 15 is a partial vertical sectional view showing the disassembled state of an embodiment of the prefilled syringe according to the present invention (first-named and second-named inventions).
Figure 16:
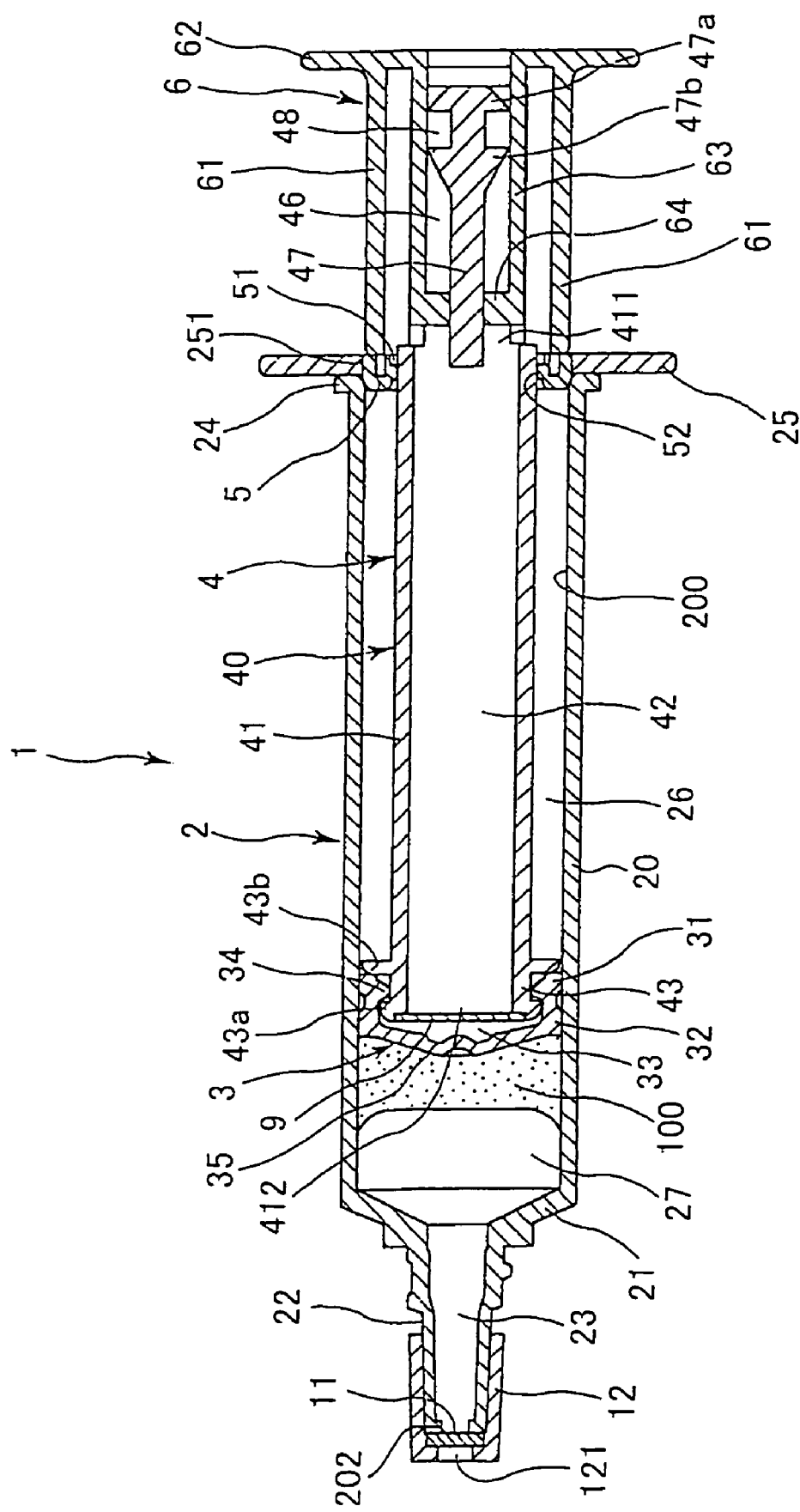
FIG. 16 is a vertical sectional view showing the assembled state (the state before use) of the prefilled syringe shown in FIG. 15.
Figure 17:
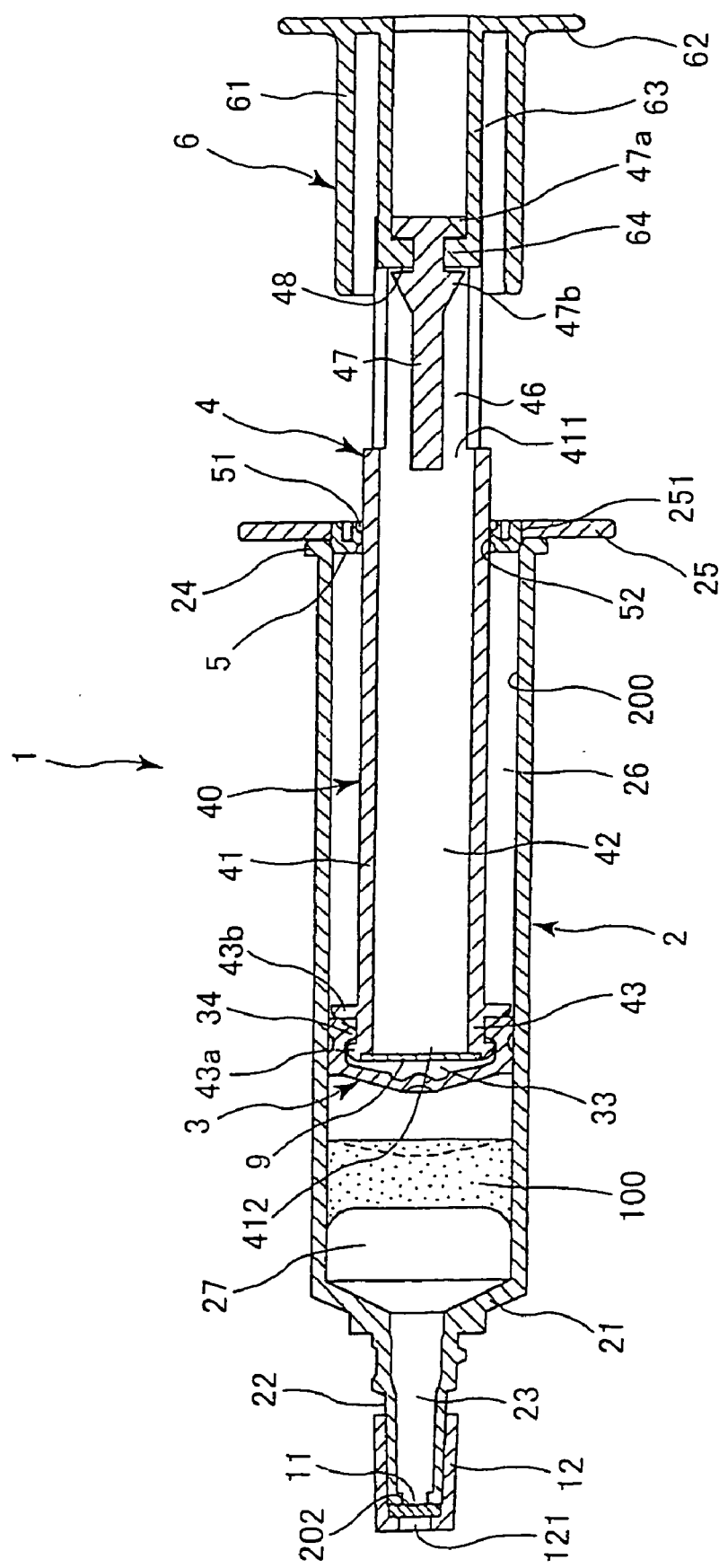
FIG. 17 is a vertical sectional view showing the assembled state (the state in use) of the prefilled syringe shown in FIG. 15.
Figure 18:
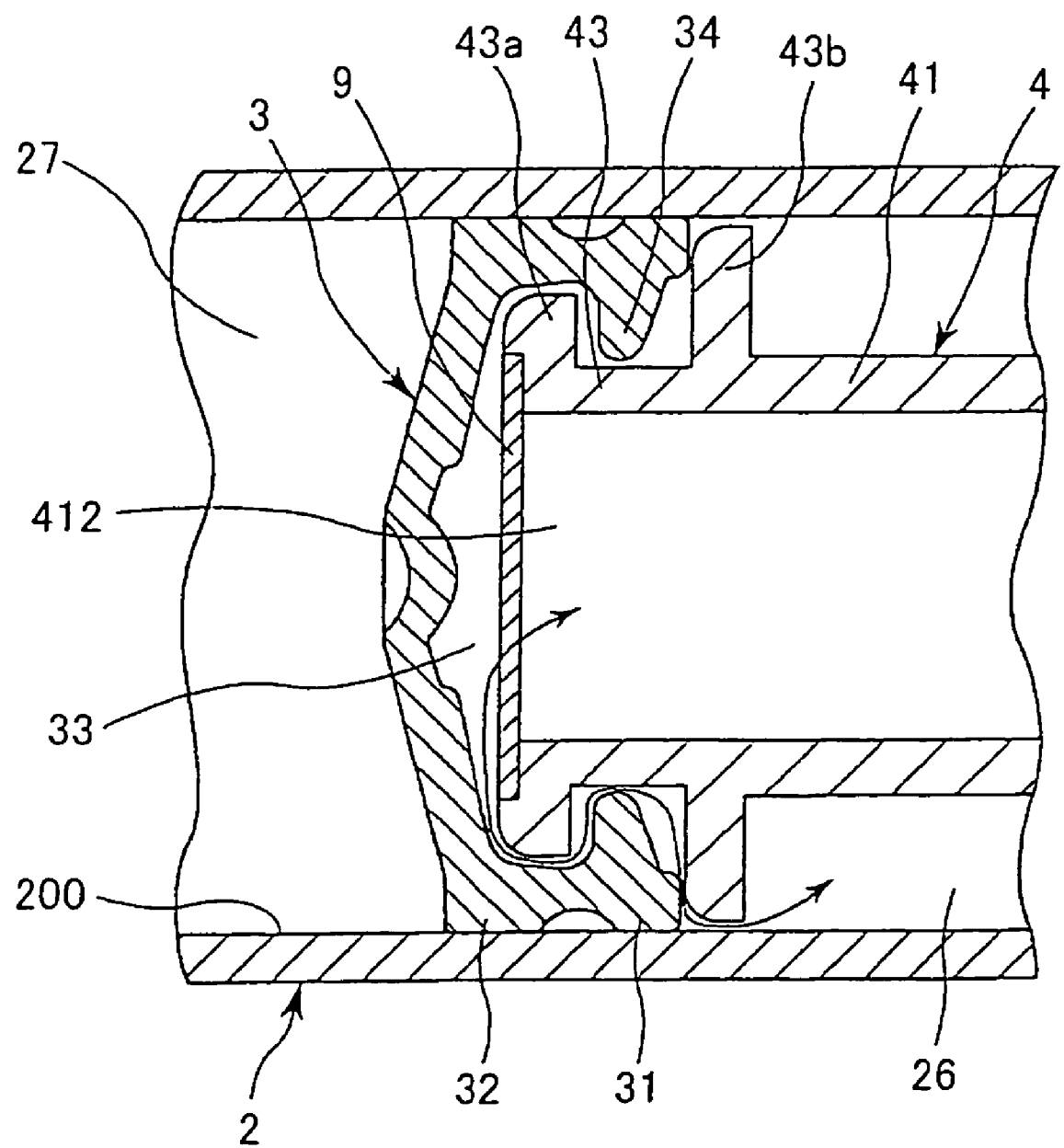
FIG. 18 is a vertical sectional view showing, in an enlarged state, the vicinity of a gasket in the prefilled syringe shown in FIG. 17.
Figure 19:
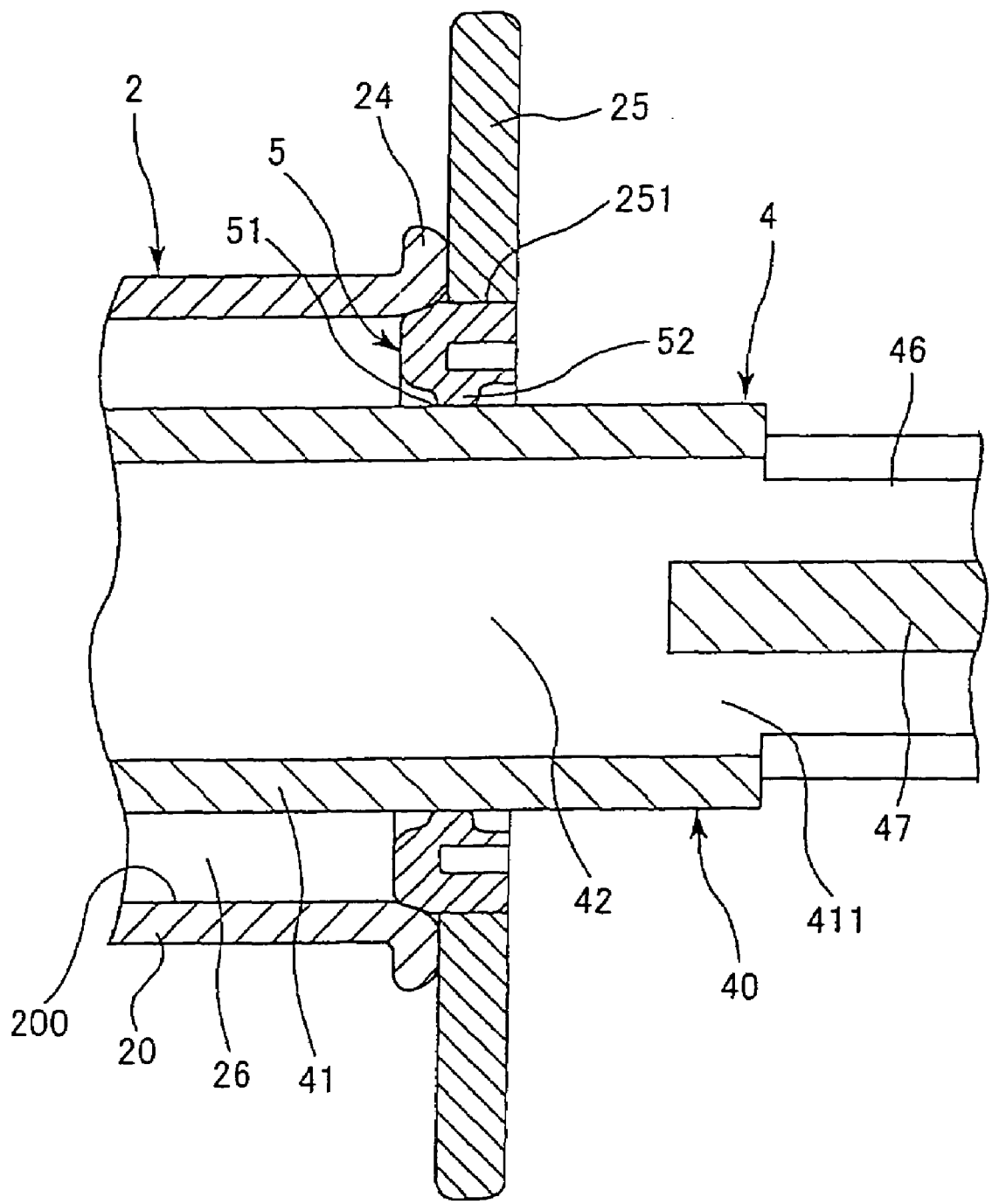
FIG. 19 is a vertical sectional view showing, in an enlarged state, the vicinity of a base end portion of an outer tube in the prefilled syringe shown in FIG. 17.

FIG. 15 is a vertical sectional view showing the disassembled state in this embodiment of the syringe (prefilled syringe); FIG. 16 is a vertical sectional view showing the assembled state (the state before use) of the syringe shown in FIG. 15; FIG. 17 is a vertical sectional view showing the assembled state (the state at the time of use) of the syringe shown in FIG. 15; FIG. 18 is a vertical sectional view showing, in an enlarged form, the vicinity of a gasket in the syringe shown in FIG. 17; and FIG. 19 is a vertical sectional view showing, in an enlarged form, the vicinity of a base end portion of an outer tube in the syringe shown in FIG. 17. In the FIGS. 15 to 19, the left side in the figures will be referred to the side of the "tip end", and the right side in the figures will be referred to the side of the "base end". In these figures, the same symbols as in FIGS. 1 to 14 denote the portions the same as or equivalent to the above-mentioned portions. In the following description, the description of the same items as those in the first-named and second-named inventions will sometimes be omitted.

Particularly, this embodiment relates to a syringe generally the same as in the above embodiments, except mainly that a sealing member 5 and a filter 9 are provided, unlike in the embodiments of the second-named invention shown in FIGS. 9 to 14. The description of the same items as in the second-named invention will be omitted, and the following description will be centered on the differences from FIGS. 9 to 14.

The syringe 1 according to this embodiment is a prefilled syringe comprising a chemical 100 preliminarily aseptically contained (sealed) in a first space 27 in an outer tube 2. The syringe 1 comprises the outer tube 2, a gasket 3 slidable in the outer tube 2, a pusher (plunger rod) 4 operated to move the gasket 3 in the longitudinal direction of the outer tube 2, the sealing member (seal ring) 5 for sealing a base end opening 201 of the outer tube 2, and the filter 9.

As shown in FIG. 19, the sealing member 5 is disposed on the inner circumference side of a hole 251 in an outer tube flange 25, to seal gas-tight the base end opening 201 of the outer tube 2, in cooperation with the outer circumference of a main body portion 40 of the pusher 4. The sealing member 5 is entirely formed of an elastic material of which examples have been mentioned in the description of the first-named invention. The sealing member 5 is provided in its central portion with an insertion hole 51 for passing a sliding portion 41 of the main body portion 40 of the pusher 4 (which will be described later) therethrough.

At the inner circumferential portion of the insertion hole 51, an annular projected portion 52 projected from the inside surface of the insertion hole 51 toward a central portion is provided over the entire circumference. The projected portion 52 slides while making close contact with the outer circumferential surface of the sliding portion 41 of the pusher 4, thereby securing gas-tightness.

In addition, the outer circumferential surface of the sealing member 5 makes gas-tight close contact with the inner circumferential surface of the hole 251 in the outer tube flange 25, and also makes gas-tight close contact with the inner circumferential surface 200 of the base end opening 201 of the outer tube 2. This ensures that the base end opening 201 of the outer tube 2 can be sealed substantially gas-tight by the sealing member 5.

The sealing member 5 is preferably one which is formed integrally with the outer tube flange 25 by two-color molding using an elastic material for constituting the sealing member 5 and a comparatively hard material for constituting the outer tube flange 25. This makes it possible to easily produce the sealing member 5, and makes it easy to assemble the syringe 1.

With the sealing member 5 thus provided, the atmospheric air is prevented from entering into the outer tube 2, and the atmospheric air is prevented from making contact with the inner circumferential surface 200, so that the aseptic property of the inside of the outer tube 2 can be maintained at a high level.

Besides, even if the syringe 1 is packaged in a non-aseptic environment after mounting the pusher 4 in assembling the syringe 1, it is unnecessary to maintain the aseptic property in the packaging step, since the aseptic property of the inside of the syringe can be maintained; therefore, provision of the sealing member 5 is advantageous on the basis of production and assembly.

In addition, the sealing member 5 also has the function of preventing the gasket 3 and the pusher 4 (described later) from slipping off from the outer tube 2.

Incidentally, the sealing member 5 may be one that is produced separately and is mounted in the base end opening 201 of the outer tube 2. Besides, the sealing member 5 may not necessarily be entirely formed of an elastic material, and it suffices that at least its portion in the vicinity of the insertion hole 51 is formed of an elastic material.

As shown in FIG. 18, the gasket 3 formed of the same elastic material as in the second-named invention is contained in the outer tube 2.

As shown in FIG. 16, in this syringe 1, a chemical 100 is preliminarily contained in a second space 27 surrounded by the outer tube 2, which is located on the tip end side of the gasket 3, and the gasket 3.

The pusher 4 to be operated to move the gasket 3 inside the outer tube 2 in the longitudinal direction is linked (attached) to the gasket 3.

As shown in FIG. 15, the pusher 4 has the main body portion (pusher main body) 40. The main body portion 40 has the sliding portion 41. As has been described above, the outer circumferential surface of the sliding portion 41 slides while making close contact with the projected portion 52 of the sealing member 5.

The sliding portion 41 is provided at its tip end with a brim-like first flange 43a and with a second flange 43b located in the vicinity of the base end side of the first flange 43a.

A portion, located on the tip end side of the second flange 43b, of the sliding portion 41 and the first flange 43a constitute a head portion 43. As shown in FIG. 18, the head portion 43 is inserted in the hollow portion 33 of the gasket 3. An engaging portion 34 projecting to the inside is formed at an inner circumferential portion near the opening of the hollow portion 33 of the gasket 3, and the engaging portion 34 is inserted between the first flange 43a and the second flange 43b. This ensures that the engaging portion 34 is engaged with the first flange 43a and the second flange 43b, whereby the gasket 3 and the pusher 4 (main body portion 40) are linked to each other.

As shown in FIG. 17, the sliding portion 41 is provided at its base end with a base end opening portion 411 for opening to the exterior. In addition, the sliding portion 41 is provided at its tip end with a tip end opening portion 412. Namely, the tip end opening 412 is located in the hollow portion 33 of the gasket 3. With this configuration, the lumen of the sliding portion 41 functions as a ventilation passage (conduit) 413 for communication between a space 26, which is surrounded by the outer tube 2 located on the base end side of the gasket 3, the gasket 3 and the sealing member 5, and the exterior.

When the pusher 4 is pushed to move (slide) the gasket 3 to the tip end direction, the atmospheric air (air in the exterior) is sucked in through the base end opening portion 411, and flows through the ventilation passage 413, the tip end opening portion 412 and through the gap between the head portion 43 and the gasket 3, into the space 26. On the contrary, when the pusher 4 is pulled to move (slide) the gasket 3 to the base end direction, air in the space 26 flows out to the exterior through a route reverse to the above. Since air in the space 26 thus freely comes in from the exterior and out to the exterior, at the times of operations to push and pull the pusher 4, the pressure inside the space 26 is not varied. Therefore, the pressure inside the space 26 will not so act as to hinder the movement of the gasket 3, so that the operation of moving the pusher 4 can be performed with a small force.

As shown in FIG. 18, when the gasket 3 is inserted in the outer tube 2 and is slightly deformed (reduced in diameter) due to the restriction by the inside diameter of the outer tube 2, a gap is formed between the inner circumferential surface of the hollow portion 33 of the gasket 3 and the head portion 43. When the pusher 4 is moved in the longitudinal direction, air flows through the gap between the head portion 43 and the gasket 3 to be thereby distributed between the space 26 and the ventilation passage 413, as indicated by arrows in FIG. 18.

Incidentally, a structure may be adopted in which cutouts are formed at portions in the circumferential direction of the first flange 43a and the second flange 43b, to provide a portion where the gap between the head portion 43 and the gasket 3 is enlarged, thereby enlarging the conduit.

The filter 9 permeable to gases but impermeable to bacteria is disposed in the tip end opening portion 412 of the sliding portion 41, and is so located as to plug up the ventilation passage 413. An outer circumferential portion of the filter 9 is fixed to the tip end opening portion 412 over the entire circumference, by such a method as fusing (heat fusing, high-frequency fusing, ultrasonic fusing, or the like), and adhesion (adhesion with an adhesive or a solvent).

When the atmospheric air flows into the space 26 in the above-mentioned manner, bacteria present in the atmospheric air are removed when passing through the filter 9. Therefore, even when the atmospheric air flows into the space 26, the bacteria are prevented from entering into the outer tube 2, and the aseptic condition inside the outer tube 2 can be maintained.

Incidentally, though the filter 9 may be disposed at an intermediate portion of the sliding portion 41 (ventilation passage 413), provision of the filter 9 in the tip end opening portion 412 promises easy production (assembly).

In addition, the position of the tip end opening of the ventilation passage 413 may not necessarily be located at the hollow portion 33 of the gasket 3. For example, a configuration may be adopted in which a pipe wall in the vicinity of the base end side of the second flange 43b of the sliding portion 41 is provided with a side hole, and the ventilation passage 413 and the space 26 are communicated with each other through the side hole. In this case, the tip end of the sliding portion 41 may be sealed up.

As shown in FIG. 15, on the base end side of the sliding portion 41, a pair of arm portions 46 as if formed by cutting out a pipe wall on the upper and lower sides in the figure from a hollow cylinder similar to the sliding portion 41 are projected to the base end direction. The pair of arm portions 46 are linked to each other by a rail portion 47 formed therebetween to extend in the longitudinal direction. The cross-sectional shapes of the pair of arm portions 46 and the rail portion 47 are so designed as to be roughly H-shaped as a whole.

The rail portion 47 is provided at its base end portion with roughly right-angled triangular projected portions 47a on the upper and lower sides in the figure. The inclined surfaces of the projected portions 47a are directed toward the base end side.

In addition, on the tip end side of the projected portions 47a, roughly right-angled triangular projected portions 47b are provided at upper end lower portions in the figure, with an interval therebetween. The inclined surfaces of the projected portions 47b are directed toward the tip end side.

Between the projected portions 47a and the projected portions 47b, roughly tetragonal recessed portions 48 are formed so as to be defined therebetween.

In this embodiment, the pusher 4 is composed of a main body portion 40 as above, and an operating portion (pusher operating portion) 6 disposed on the base end side of the main body portion 40 so as to be movable in the longitudinal direction of the pusher 4, and the length (overall length) of the pusher 4 is variable (contractible and extendable). Such a structure of the pusher 4 composed of the main body portion 40 and the operating portion 6 and the contraction/expansion actions thereof are the same as in the second-named invention, and the description thereof is therefore omitted here. By the movements of the operating portion 6, the length of the pusher 4 is varied (contracted and extended) between a short state shown in FIG. 16 and a long state shown in FIG. 17.

With the length of the pusher 4 variable, the overall length of the syringe 1 in the pre-use state of the syringe 1 shown in FIG. 16 can be reduced, and, therefore, the space required during transportation and storage of the syringe 1 can be reduced.

When the operating portion 6 is moved to the base end direction relative to the main body portion 40 starting from the condition shown in FIG. 16, both the projected portions 64 slide along the inclined surfaces of both the projected portions 47b, whereby both the elastic pieces 63 are elastically deformed so as to open wider, and, concurrently, both the projected portions 64 ride over both the projected portions 47b to be inserted (fitted) into both the recessed portions 48, respectively, resulting in the condition shown in FIG. 17. In this condition, both the projected portions 64 and both the recessed portions 48 are engaged with each other (fitted to each other), whereby the pusher 4 can be maintained (held) in a long state. Thus, the projected portions 47a, 47b, the recessed portions 48 and the elastic pieces 63 constitute maintaining means for maintaining the long state of the pusher 4.

In the pre-use condition of the syringe 1 shown in FIG. 16, the pusher 4 is kept in the short state, and the gasket 3 is located on the base end side of the chemical 100. In this condition, even if the operating portion 6 is pushed to the tip end direction, it is impossible to move the gasket 3 further to the tip end direction, since a tip end portion of the operating portion 6 (hollow cylindrical portion 61) abuts on the base end face of the sealing member 5 (or the outer tube flange 25); therefore, it is impossible to push the gasket 3 up to the tip end portion (bottom portion 21) of the barrel portion 20 of the outer tube 2. Therefore, even when a force for pushing the pusher 4 (operating portion 6) is exerted by mistake before the use of the syringe 1 (during transportation or storage), the gasket 3 cannot be moved to the tip end direction. This has the following merits (1) to (3), like in the second-named invention.

(1) The chemical 100 can be stored without breaking the shape thereof, and the beautiful appearance of the product can be maintained securely.

(2) If the gasket 3 is moved to the tip end direction unlike in this embodiment, the chemical 100 collapsed into a powdery form may enter into the gap between the outer circumferential surface of the gasket 3 and the inner circumferential surface 200 of the outer tube 2. In that case, even when the chemical 100 is thereafter dissolved by sucking in an infusion, the chemical 100 having entered the gap between the outer circumferential surface of the gasket 3 and the inner circumferential surface 200 of the outer tube 2 is left undissolved, resulting in an error in the amount of the chemical 100 injected. In this embodiment, generation of such a trouble can be prevented assuredly.

(3) If the gasket 3 can be moved to the tip end direction before use, unlike in this embodiment, when the pusher 4 is pushed by mistake, particularly where the chemical 100 is a liquid, the pressure of the liquid (liquid chemical 100) would be raised, so that the liquid may leak through the reduced-diameter portion 22 by breaking the membrane 11, or the liquid may leak through the gap between the inner circumferential surface 200 of the outer tube 2 and the gasket 3 into the space 26. On the other hand, in this embodiment, generation of such a trouble can be prevented securely.

In the syringe 1 according to this embodiment as above, at the time of use, the pusher 4 is set in the long state, as shown in FIG. 17, whereby it is ensured that the pusher 4 is sufficiently long, and the gasket 3 can be pushed up to the tip end portion (bottom portion 21) of the barrel portion 20 of the outer tube 2. Specifically, when the pusher 4 is pushed and moved further to the tip end direction starting from the condition shown in FIG. 17, the tip end face of the gasket 3 makes contact with (abuts on) the inside surface of the bottom portion 21, whereas the tip end portion of the operating portion 6 (hollow cylindrical portion 61) does not make contact with (abut on) the base end face of the sealing member 5 (or the outer tube flange 25).

Incidentally, in this embodiment, the pusher 4 may be one of which the length is not variable.

The method of using the syringe 1 in this embodiment is basically the same as [1] to [4] described above as one example of mixingly injecting a liquid chemical into an infusion container (not shown) according to the second-named invention.

Thus, in the case where a prefilled syringe such as the syringe 1 in this embodiment is used, at the time of mixingly injecting the chemical 100 or at the time of performing injection, the operation can be carried out in an aseptic manner as above-described, the risk of infection can be reduced, there is no need for replacement of the container, and contamination of the chemical and taking one chemical for another can be prevented securely.

While the embodiments shown in the figures of the syringe according to the present invention have been described above, the present invention is not limited to the above embodiments. The configurations of the components of the syringe, particularly, the pusher, the gasket, the sealing member, and the ventilation means are not limited to those shown in the figures, and can be arbitrary ones that can display the same functions as above-mentioned. Besides, arbitrary components may be added.

In addition, while the present invention has been described above based on the embodiments of a prefilled syringe, the syringe according to the present invention is not limited to the prefilled syringe, and may be an ordinary syringe in which a chemical is not preliminarily contained.

INDUSTRIAL APPLICABILITY

As has been described above, according to the syringe structure of the present invention, it is possible to secure the sanitation of the inside of a syringe outer tube when not in use, to easily perform the operations of discharging (injecting) a liquid chemical and the like, and to thereby provide excellent operability.

Specifically, the operation of pushing or pulling a pusher can be performed with a small force, and the aseptic property of the inside of the syringe can be securely maintained even when a gasket is slid to the tip end direction and to the base end direction. Particularly, a prefilled syringe according to the present invention is high in inside aseptic property keeping performance, and is excellent in sanitation and safety.

The syringe in the mode including the second-named invention has such a configuration that when the pusher is in its short state, the gasket can be prevented from being moved to the tip end direction even if the pusher is pushed. Therefore, when the present invention is applied to a syringe in which a chemical is preliminarily contained in the space surrounded by the tip end face of the gasket and the outer tube, even if the pusher is pushed by some force exerted before use, the gasket would not be moved to the tip end direction, and generation of a trouble attendant on movement of the gasket can be prevented assuredly.

The invention claimed is:

1. A syringe comprising:
   an outer tube provided on the tip end side thereof with a mouth portion permitting a liquid to come in and out therethrough;
   a gasket slidable in said outer tube;
   a pusher connected to said gasket and operated to move said gasket in the longitudinal direction of said outer tube;
   a ventilation means provided in said pusher; and
   a sealing member sealing a base end opening of said outer tube and having an insertion hole for inserting said pusher therethrough;
   wherein a first space surrounded by said outer tube and said gasket and located on the tip end side of said gasket, and a second space surrounded by said outer tube, said gasket and said sealing member and located on the base end side of said gasket are provided in said outer tube, and
   before an operation to push said pusher to the tip end direction, said second space is maintained in the state of being shielded (sealed) from the outside air and, when the operation to push said pusher to the tip end direction is performed, the outside air is let into said second space by said ventilation means.

2. A syringe as set forth in claim 1, wherein said ventilation means is a groove or slit opening to the outer circumferential surface of said pusher.

3. A prefilled syringe as set forth in claim 1, wherein said ventilation means is comprised of a ventilation passage formed inside said pusher to open, at one end thereof, to said outer circumferential surface of said pusher.

4. A syringe as set forth in claim 1, wherein said ventilation means is a rib formed on said outer circumferential surface of said pusher.

5. A syringe as set forth in claim 1, wherein the pressure difference $P_1-P_2$ is not more than 0.9 atm, where $P_1$ [atm] is the pressure in said second space before the start of the operation to push said pusher to the tip end direction, and $P_2$ [atm] is the pressure in said second space after said operation to push said pusher to the tip end direction is started and immediately before the outside air is let into said second space.

6. A syringe as set forth in claim 1, wherein the moving distance of said pusher from the time when said operation to push said pusher to the tip end direction is started till the time when the outside air is let into said second space is in the range of 2 to 10 mm.

7. A syringe comprising:
   an outer tube provided on the tip end side thereof with a mouth portion permitting a liquid to come in and out therethrough;
   a gasket slidably disposed in said outer tube and partitioning the inside of said outer tube into the tip end side and the base end side;
   a pusher connected to said gasket and operated to move said gasket in the longitudinal direction of said outer tube;
   a ventilation passage formed inside said pusher so as to communicate a second space surrounded by said outer tube, said gasket and said sealing member and located on the base end side of said gasket and the exterior to each other;
   a sealing member sealing a base end opening of said outer tube and having an insertion hole for inserting said pusher therethrough; and
   a filter disposed so as to shut off said ventilation passage, and permitting gases to pass therethrough but not permitting bacteria to pass therethrough;
   wherein when said pusher is moved to the tip end direction, the outer circumferential surface of said pusher slides while making close contact with at least a part of said insertion hole, and the outside air is let into said space through said ventilation passage.

8. A syringe as set forth in claim 7, wherein at least a portion, in the vicinity of said ventilation hole, of said sealing member is formed of an elastic material.

9. A syringe as set forth in claim 7, wherein said gasket is provided with a hollow portion opening to a base end face thereof, said pusher is provided at a tip end portion thereof with a head portion to be inserted into said hollow portion, and a tip end opening portion of said ventilation passage is formed in said head portion.

10. A syringe as set forth in claim 9, wherein said filter is provided at said tip end opening portion of said ventilation passage.

11. A syringe as set forth in claim 9, wherein when said pusher is moved in the longitudinal direction thereof, air is distributed between said space and said ventilation passage through a gap between said head portion and said gasket.

12. A syringe comprising: an outer tube provided on the tip end side thereof with a mouth portion permitting a liquid to come in and out therethrough; a gasket slidably disposed in said outer tube and partitioning the space in said outer tube into the tip end side and the base end side; and a pusher connected to said gasket and operated to move said gasket in the longitudinal direction of said outer tube, wherein said pusher comprises a pusher main body, and a pusher operating portion disposed on the base end side of said pusher main body so as to be movable in the longitudinal direction of said pusher, said pusher operating portion has an abutment portion abutting on a base end portion, or a portion near said base end portion, of said outer tube in the condition where the length of said pusher is small, and in the condition where the length of said pusher is small, said abutment portion abuts on said base end portion, or the portion near said base end portion, of said outer tube, whereby said gasket is prevented from being pushed to a tip end portion of a barrel portion of said outer tube, but in the condition where the length of said pusher is large, said gasket can be pushed to said tip end portion of said barrel portion of said outer tube.

13. A syringe as set forth in claim 12, comprising maintaining means for maintaining the condition where said length of said pusher is large.

14. A syringe as set forth in claim 13, wherein either one of said pusher main body and said pusher operating portion comprises an elastic piece, and a projected portion formed on the opposite side of the base of said elastic piece, while the other of said pusher main body and said pusher operating portion has a recessed portion into which said projected portion can be inserted, and in the condition where the length of said pusher is large, said projected portion is inserted into and engaged with said recessed portion by the elasticity of said elastic piece, whereby the condition where the length of said pusher is large is maintained.

15. A syringe as set forth in claim 12, comprising a chemical contained in a space surrounded by said outer tube and said gasket and located on the tip end side of said gasket.

16. A syringe as set forth in claim 12, comprising a plate-like outer tube flange at a base end portion of said outer tube, wherein said abutment portion abuts on a base end face of said outer tube flange in the condition where the length of said pusher is small.

17. A prefilled syringe comprising a chemical contained in a space on the tip end side of said gasket in a syringe as set forth in claim 1.

* * * * *